US009113851B2

(12) United States Patent
Agnew

(10) Patent No.: US 9,113,851 B2
(45) Date of Patent: Aug. 25, 2015

(54) FISTULA PLUGS AND APPARATUSES AND METHODS FOR FISTULA PLUG DELIVERY

(75) Inventor: Charles W. Agnew, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 1675 days.

(21) Appl. No.: 12/179,366

(22) Filed: Jul. 24, 2008

(65) Prior Publication Data
US 2009/0054927 A1 Feb. 26, 2009

Related U.S. Application Data

(60) Provisional application No. 60/957,581, filed on Aug. 23, 2007.

(51) Int. Cl.
*A61B 17/08* (2006.01)
*A61B 17/00* (2006.01)
(Continued)

(52) U.S. Cl.
CPC ....... *A61B 17/0057* (2013.01); *A61B 17/12159* (2013.01); *A61B 17/12168* (2013.01); *A61F 2/0004* (2013.01); *A61F 2/0009* (2013.01);
(Continued)

(58) Field of Classification Search
CPC .............. A61B 17/0057; A61B 17/12168; A61B 17/12022; A61B 17/12159; A61B 2017/12054; A61B 2017/00641; A61B 2017/00004; A61B 2017/00659; A61F 2/0009; A61F 2/0004; A61F 2/0013; A61F 2002/045
USPC .......... 606/213, 215, 216, 197; 128/898, 887; 600/30; 623/23.64
See application file for complete search history.

(56) References Cited

U.S. PATENT DOCUMENTS 2,127,903 A 3/1938 Bowen
4,511,653 A 4/1985 Play et al.
(Continued)

FOREIGN PATENT DOCUMENTS

EP 1570788 9/2005
EP 1671591 6/2006
(Continued)

OTHER PUBLICATIONS

Himpson, Rebecca C. et al., "Histological evidence for enhanced anal fistula repair using autologous fibroblasts in a dermal collagen matrix," Comparative Clinical Pathology, Apr. 2006, vol. 16, No. 1.
(Continued)

*Primary Examiner* — Jing Ou
(74) *Attorney, Agent, or Firm* — Woodard, Emhardt, Moriarty, McNett & Henry LLP

(57) ABSTRACT

Described are methods and apparatuses for delivering fistula plugs into fistulae having at least a primary fistula opening, a secondary fistula opening, and a fistula tract extending therebetween. Illustratively, some inventive methods involve delivering a fistula plug into a fistula tract through a primary fistula opening and toward a secondary fistula opening, while others involve delivering a fistula plug into a fistula tract through a secondary fistula opening and toward a primary fistula opening. In certain aspects, a fistula plug is pushed and/or pulled through a fistula tract along a guidewire or other plug-guiding device, potentially protected by a protective delivery device such as a sheath, capsule or other suitable delivery vehicle.

41 Claims, 9 Drawing Sheets

(51) Int. Cl.
*A61F 2/00* (2006.01)
*A61F 2/04* (2013.01)
*A61B 17/12* (2006.01)

(52) U.S. Cl.
CPC ......... *A61F 2/0013* (2013.01); *A61B 17/12022* (2013.01); *A61B 2017/00004* (2013.01); *A61B 2017/00641* (2013.01); *A61B 2017/00659* (2013.01); *A61B 2017/12054* (2013.01); *A61F 2002/045* (2013.01)

(56) References Cited

U.S. PATENT DOCUMENTS

| | | | |
|---|---|---|---|
| 4,758,219 A * | 7/1988 | Sacks et al. | 604/506 |
| 4,902,508 A | 2/1990 | Badylak et al. | |
| 4,956,178 A | 9/1990 | Badylak et al. | |
| 4,981,465 A | 1/1991 | Ballan | |
| 5,084,014 A * | 1/1992 | Picha et al. | 604/500 |
| 5,112,310 A * | 5/1992 | Grobe | 604/175 |
| 5,192,302 A | 3/1993 | Kensey et al. | |
| 5,222,970 A | 6/1993 | Reeves | |
| 5,275,826 A | 1/1994 | Badylak et al. | |
| 5,281,422 A | 1/1994 | Badylak et al. | |
| 5,297,536 A * | 3/1994 | Wilk | 600/104 |
| 5,304,123 A | 4/1994 | Atala et al. | |
| 5,334,216 A | 8/1994 | Vidal | |
| 5,374,261 A | 12/1994 | Yoon | |
| RE34,866 E | 2/1995 | Kensey | |
| 5,411,475 A | 5/1995 | Atala et al. | |
| 5,516,533 A | 5/1996 | Badylak et al. | |
| 5,554,389 A | 9/1996 | Badylak et al. | |
| 5,584,827 A | 12/1996 | Korteweg et al. | |
| 5,620,461 A | 4/1997 | Muijs Van De Moer | |
| 5,628,762 A | 5/1997 | Al-Tameem | |
| 5,643,305 A | 7/1997 | Al-Tameem | |
| 5,752,974 A | 5/1998 | Rhee et al. | |
| 5,755,791 A | 5/1998 | Whitson et al. | |
| 5,779,672 A | 7/1998 | Dormandy | |
| 5,830,228 A | 11/1998 | Knapp et al. | |
| 5,904,703 A * | 5/1999 | Gilson | 606/213 |
| 5,955,110 A | 9/1999 | Patel et al. | |
| 5,993,844 A | 11/1999 | Abraham et al. | |
| 5,997,575 A | 12/1999 | Whitson et al. | |
| 6,090,996 A | 7/2000 | Li | |
| 6,099,567 A | 8/2000 | Badylak et al. | |
| 6,126,686 A | 10/2000 | Badylak et al. | |
| 6,159,243 A * | 12/2000 | Schouwenburg | 623/9 |
| 6,206,931 B1 | 3/2001 | Cook et al. | |
| 6,220,336 B1 | 3/2001 | Badylak et al. | |
| 6,315,787 B1 | 11/2001 | Tsugita | |
| 6,375,989 B1 | 4/2002 | Badylak et al. | |
| 6,569,081 B1 | 5/2003 | Nielsen et al. | |
| 6,666,892 B2 | 12/2003 | Hiles | |
| 7,485,087 B2 * | 2/2009 | Burgard | 600/32 |
| 2002/0072744 A1 * | 6/2002 | Harrington et al. | 606/41 |
| 2002/0143346 A1 * | 10/2002 | McGuckin et al. | 606/139 |
| 2003/0013989 A1 | 1/2003 | Obermiller et al. | |
| 2003/0051735 A1 * | 3/2003 | Pavcnik et al. | 128/831 |
| 2003/0100920 A1 * | 5/2003 | Akin et al. | 606/213 |
| 2003/0135234 A1 * | 7/2003 | Fisher et al. | 606/213 |
| 2004/0158185 A1 | 8/2004 | Moran et al. | |
| 2004/0176798 A1 | 9/2004 | Epstein et al. | |
| 2005/0013844 A1 | 1/2005 | Hadlock et al. | |
| 2005/0049626 A1 * | 3/2005 | Burgard | 606/191 |
| 2005/0059990 A1 * | 3/2005 | Ayala et al. | 606/192 |
| 2005/0070759 A1 | 3/2005 | Armstrong | |
| 2005/0155608 A1 | 7/2005 | Pavcnik et al. | |
| 2005/0159776 A1 | 7/2005 | Armstrong | |
| 2005/0182495 A1 | 8/2005 | Perrone | |
| 2006/0015142 A1 | 1/2006 | Malazgirt | |
| 2006/0212055 A1 * | 9/2006 | Karabey et al. | 606/158 |
| 2006/0241688 A1 * | 10/2006 | Wilk | 606/213 |
| 2007/0016172 A1 * | 1/2007 | Charukhchian | 606/1 |
| 2007/0031508 A1 * | 2/2007 | Armstrong et al. | 424/572 |
| 2007/0088445 A1 * | 4/2007 | Patel et al. | 623/23.64 |
| 2007/0129757 A1 * | 6/2007 | Armstrong | 606/213 |
| 2007/0179507 A1 * | 8/2007 | Shah | 606/113 |
| 2007/0198059 A1 * | 8/2007 | Patel et al. | 606/213 |
| 2008/0004657 A1 * | 1/2008 | Obermiller et al. | 606/213 |
| 2008/0051831 A1 * | 2/2008 | Deal et al. | 606/213 |

FOREIGN PATENT DOCUMENTS

| | | |
|---|---|---|
| RU | 2180529 | 3/2002 |
| WO | WO 93/07813 | 4/1993 |
| WO | WO 98/25637 | 6/1998 |
| WO | WO 98/56290 | 12/1998 |
| WO | WO 00/19912 | 4/2000 |
| WO | WO 00/72759 | 12/2000 |
| WO | WO 2004/012627 | 2/2004 |
| WO | WO 2005/020823 | 3/2005 |
| WO | WO 2005/020847 | 3/2005 |
| WO | WO 2005/070302 | 8/2005 |
| WO | WO 2007/002260 | 1/2007 |
| WO | WO 2007/011443 | 1/2007 |
| WO | WO 2007/064819 | 6/2007 |
| WO | WO 2007/090150 | 8/2007 |
| WO | WO 2007/090155 | 8/2007 |

OTHER PUBLICATIONS

Khairy, G.E.A., et al., "Percutaneous obliteration of duodenal fistula," J.R. Coll. Surg. Edinb., 45 Oct. 2000, 342-344.

Lisle, David A., et al., "Percutaneous Gelfoam Embolization of Chronic Enterocutaneous Fistulas: Report of Three Cases," Diseases of the Colon & Rectum, vol. 50, No. 2, Dec. 2006.

Maluf-Fiho, F., et al., "Endoscopic Treatment of Esophagogastric Fistulae with an Acellular Matrix," Gastrointestinal Endoscopy, Elsevier, NL, vol. 59, No. 5, Apr. 2004, p. 151, XP004854594 abstract.

Miklos, J.R., et al., "Rectovaginal Fistula Repair Utilizing a Cadaveric Dermal Allograft," International Urogynecology Journal, 1999, vol. 10, No. 6, pp. 405-406.

Moore, Robert D., et al., "Rectovaginal Fistula Repair Using a Porcine Dermal Graft," Obstetrics & Gynecology, 2004, 104, 1165-1167.

Schultz, David J., et al., "Porcine Small Intestine Submucosa as a Treatment for Enterocutaneous Fistulas,"Journal of American Collage of Surgeons, 2002, vol. 194, No. 4, Apr. 2002, pp. 541-543.

Schwesinger, Wayne H., "Management of Persistent Fistula After Gastrectomy", on-line question(www.medscape.com), posted on May 14, 2002.

Shah, A.M., et al., "Bronchoscopic closure of bronchopleural fistula using gelfoam," Abstract, Journal of Association of Physicians of India, 2004, vol. 52, n JUIN, pp. 508-509.

Shaker MA, et al., "Competent Closure of Chronic Oroantral Fistula with Zenoderm," Egypt Dent J. Jul. 1995; 41(3):1237-42.

Sheiman, Robert G. et al., "Percutaneous Treatment of a Pancreatic Fistula after Pancreaticoduodenectomy," J Vasc Interv Radiol, 2001, vol. 12, No. 4, pp. 524-526.

Shelton, Andrew A., et al., Transperineal Repair of Persistent Rectovaginal Fistulas Using an Acellular Cadaveric Dermal Grant (AlloDerm®). Diseases of the Colon & rectum, Sep. 2006, vol. 49, No. 9.

Wilson Gunn on behalf of unnamed party, Letter to the European Patent Office, Jan. 30, 2007, pp. 1-4.

* cited by examiner

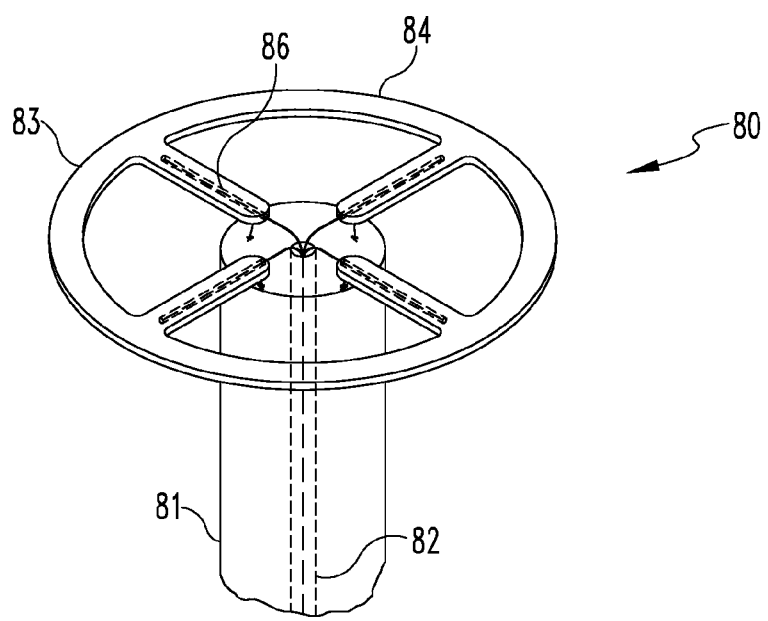
Fig. 9A
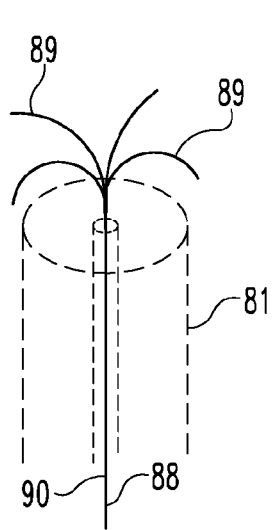 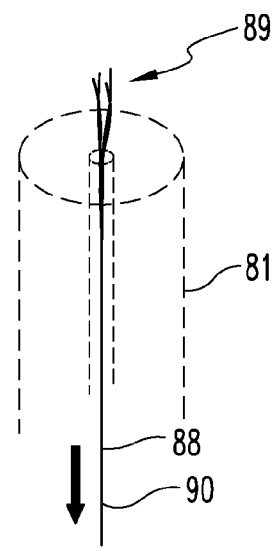
Fig. 9B          Fig. 9C

FISTULA PLUGS AND APPARATUSES AND METHODS FOR FISTULA PLUG DELIVERY

REFERENCE TO RELATED APPLICATION

The present application claims the benefit of U.S. Provisional Patent Application Ser. No. 60/957,581 filed Aug. 23, 2007, entitled "Fistula Plugs and Apparatuses and Methods for Fistula Plug Delivery" which is hereby incorporated by reference in its entirety.

BACKGROUND

The present invention relates generally to medical devices and in particular aspects to apparatuses and methods for treating fistulae.

As further background, fistulae can occur for a variety of reasons such as but not limited to as a congenital defect, as a result of inflammatory bowel disease such as Chron's disease, irradiation, trauma such as childbirth, or as a side effect from a surgical procedure. Additionally, several different types of fistulae can occur in humans, for example, urethro-vaginal fistulae, vesico-vaginal fistulae, tracheo-esophageal fistulae, gastrointestinal fistulae including but not limited to gastrocutaneous, enterocutaneous and colocutaneous fistulae, and any number of anorectal fistulae such as recto-vaginal fistula, recto-vesical fistulae, recto-urethral fistulae, and recto-prostatic fistulae.

A gastrointestinal fistula is an abnormal passage that leaks contents of the stomach or the intestine (small or large bowel) to other organs, usually other parts of the intestine or the skin. For example, gastrojejunocolic fistulae include both enterocutaneous fistulae (those occurring between the skin surface and the intestine, namely the duodenum, the jejunum, and the ileum) and gastric fistulae (those occurring between the stomach and skin surface). Another type of fistula occurring in the gastrointestinal tract is an enteroenteral fistula, which refers to a fistula occurring between two parts of the intestine. Gastrointestinal fistulae can result in malnutrition and dehydration depending on their location in the gastrointestinal tract. They can also be a source of skin problems and infection. The majority of these types of fistulae are the result of surgery (e.g., bowel surgery), although sometimes they can develop spontaneously or from trauma, especially penetrating traumas such as stab wounds or gunshot wounds. Inflammatory processes, such as infection or inflammatory bowel disease (Crohn's disease), may also cause gastrointestinal fistulae. In fact, Crohn's disease is the most common primary bowel disease leading to enterocutaneous fistulae, and surgical treatment may be difficult because additional enterocutaneous fistulae develop in many of these patients postoperatively.

The path which fistulae take, and their complexity, can vary. A fistula may take a take a "straight line" path from a primary opening to a secondary opening, known as a simple fistula. Alternatively, a fistula may comprise multiple tracts ramifying from a primary opening and have multiple secondary openings. This is known as a complex fistula.

Current treatment options for gastrointestinal fistulae vary. Depending on the clinical situation, patients may receive IV nutrition and go a period of time without food to try to get the fistula to close on its own. Indeed, nonsurgical therapy may allow spontaneous closure of the fistula, although this can be expected less than 30% of the time according to one estimate. A variable amount of time to allow spontaneous closure of fistulae has been recommended, ranging from 30 days to 6 to 8 weeks. During this time, external control of the fistula drainage can prevent skin disruption and provide a guideline for fluid and electrolyte replacement. In some cases, surgery is necessary to remove the segment of intestine involved in a non-healing fistula.

When surgery is deemed necessary, one operation for fistula closure is resection of the fistula-bearing segment and primary end-to-end anastamosis. The anastomosis may be reinforced by greater omentum or a serosal patch from adjacent small bowel. Still other methods for treating fistulae involve injecting sclerosant or sealant (e.g., collagen or fibrin glue) into the tract of the fistula to block the fistula. Closure of a fistula using a sealant is typically performed as a two-stage procedure, including a first-stage seton placement and injection of the fibrin glue several weeks later. This allows residual infection to resolve and to allow the fistula tract to "mature" prior to injecting the sealant. If sealant or sclerosant were injected as a one-stage procedure into an "unprepared" or infected fistula, this may cause a flare-up of the infection and even further abscess formation.

There remain needs for improved and/or alternative fistula plugs, as well as apparatuses and methods for delivering fistula plugs into the body. The present invention is addressed to those needs.

SUMMARY

The present invention provides, in certain aspects, unique methods for treating a fistula having at least a primary fistula opening in the alimentary canal, a secondary fistula opening, and a fistula tract extending therebetween. One such method comprises: (i) providing a plug-guiding device configured to traverse the fistula tract and a portion of the alimentary canal; (ii) providing a fistula plug translatable along the plug-guiding device and having sufficient column strength to be pushed through the fistula tract; (iii) positioning the plug-guiding device through the fistula tract and through a portion of the alimentary canal; (iv) associating the fistula plug with the plug-guiding device; (v) delivering the fistula plug along the plug-guiding device through the alimentary canal and to the primary fistula opening; and (vi) pushing the fistula plug along the plug-guiding device through the fistula tract toward the secondary fistula opening. The fistula plug can be delivered to the primary fistula opening in any suitable manner including some that involve pushing and/or pulling the fistula plug through the alimentary canal along the plug-guiding device. In some aspects, the plug-guiding device is a guidewire, and associating the fistula plug with the guidewire involves receiving at least part of the fistula plug over the wire. Additionally, there are a variety of ways to position the plug-guiding device through the fistula tract and through a portion of the alimentary canal. Illustratively, a first elongate device can be passed through the secondary fistula opening and through the fistula tract to a point at or near the primary fistula opening, and a second elongate device can be advanced to the same point by passing it through a natural body opening and through the alimentary canal. Thereafter, in some embodiments, the two elongate devices are united to provide a suitable plug-guiding device. In some instances, the two wires are united, and then one of the wires is withdrawn back out of the body in the direction from which it came, pulling the other wire therealong. The wire remaining in the body is then available as a plug-guiding device. Passing the second elongate device through a natural body opening and through the alimentary canal can be accomplished in a variety of manners, and in some instances, will involve the use of an endoscope. Such methods are particularly useful in treating fistulae that are difficult to access without the use of such equipment such as those that have fistula openings occurring in the stomach, intestines and other hard-to-reach locations in the body (e.g., in the bladder, urethra, etc.), and those having relatively longer and/or more complex fistula tracts.

In another embodiment, the invention provides a method of treating a fistula having at least a primary fistula opening in the alimentary canal, a secondary fistula opening, and a fistula tract extending therebetween. This method comprises: (i) providing a plug-guiding device configured to traverse the fistula tract and a portion of the alimentary canal; (ii) providing a delivery device having a lumen, the delivery device translatable along the plug-guiding device; (iii) providing a fistula plug; (iv) positioning the plug-guiding device through the fistula tract and through a portion of the alimentary canal; (v) associating the delivery device with the plug-guiding device; (vi) advancing the delivery device along the plug-guiding device through the alimentary canal and to the primary fistula opening with the fistula plug residing in the delivery device lumen; and (vii) delivering the fistula plug along the plug-guiding device through the primary fistula opening and into the fistula tract. The fistula plug may or may not continue to reside in the delivery device lumen as it is delivered into the fistula tract. In embodiments that involve directly or indirectly pushing the fistula plug along the plug-guiding device, the plug and/or a device being used in its delivery (if present) will have sufficient column strength to be so pushed.

One aspect of the present invention provides a system for delivering a fistula plug into a fistula tract, the fistula tract communicating with a first fistula opening and second fistula opening. This system comprises a delivery apparatus and a fistula plug translatable along the delivery apparatus. The delivery apparatus is configured to traverse the fistula tract, and includes a pushing element contacting the fistula plug in a first location and a pulling element coupled to the fistula plug at a second location spaced from the first location. The pushing element and the pulling element are effective to advance the fistula plug through the fistula tract from the first fistula opening toward the second fistula opening.

Another aspect of the invention provides a method for delivering a fistula plug into a fistula tract, the fistula tract communicating with a first fistula opening and second fistula opening. This method includes the provision of a fistula plug delivery system such as that described above. The delivery apparatus is positioned in the fistula tract. The fistula plug is associated with the delivery apparatus, wherein the pushing element contacts the fistula plug in a first location, and the pulling element is coupled to the fistula plug at a second location spaced from the first location. The fistula plug is delivered into the fistula tract along the delivery apparatus, wherein the fistula plug is advanced through the fistula tract from the first fistula opening toward the second fistula opening with the pushing element and the pulling element.

A further embodiment of the invention provides a method for treating a fistula having at least a primary fistula opening in the alimentary canal, a secondary fistula opening, and a fistula tract extending therebetween. This method comprises: (i) providing a retrieving device having a distal portion; (ii) providing a plug-guiding device having a distal portion and a proximal portion; (iii) providing a fistula plug; (iv) advancing the retrieving device distal portion through the fistula tract from the secondary fistula opening to the primary fistula opening; (v) advancing the plug-guiding device distal portion through the alimentary canal and to the primary fistula opening; (vi) coupling the plug-guiding device distal portion to the retrieving device distal portion; (vii) withdrawing the retrieving device distal portion back through the fistula tract from the primary fistula opening to the secondary fistula opening, wherein the coupled plug-guiding device distal portion is pulled therealong to the secondary fistula opening; (viii) associating the fistula plug with the plug-guiding device proximal portion; and (ix) delivering the fistula plug while associated with the plug-guiding device through the alimentary canal and into the fistula tract through the primary fistula opening. The fistula plug can be associated with the plug-guiding device in a variety of fashions including some that involve coupling the plug to a device component that can be used to pull the plug through the body. Additionally or alternatively, the plug (when suitably configured) can be associated with the plug-guiding device in a manner that enables the plug to translate along the plug-guiding device. Such a plug can then be pushed and/or pulled through the body along the plug-guiding device.

The present invention also provides, in another embodiment, a method of treating a fistula having at least a primary fistula opening, a secondary fistula opening, and a fistula tract extending therebetween. In this method, a first elongate device, a second elongate device and a fistula plug are provided. The first elongate device and the second elongate device each have a distal portion and a proximal portion. In some instances, the first elongate device and/or the second elongate device will be or include a wire guide or other similar elongate device capable of being advanced to the required locations in the body. The distal portion of the first elongate device is advanced through the fistula tract from the secondary fistula opening to a point at or near the primary fistula opening (e.g., to a point just beyond the primary opening). The distal portion of the second elongate device is advanced through a natural body opening to the point at or near the primary fistula opening. The primary opening, in some cases, will be in a wall of the alimentary canal, and thus, the second elongate device will be advanced into and through the alimentary canal to the primary opening. The distal portion of the first elongate device and the distal portion of the second elongate device are then joined to provide a plug-guiding device along which the fistula plug can be advanced. The fistula plug is then associated with the plug-guiding device, although in some forms, the fistula plug will already be associated with one of the elongate devices before the two distal portions are joined. The fistula plug, while associated with the plug-guiding device, is then delivered into the fistula tract, for example, through the primary fistula opening or the secondary fistula opening. In some cases, the fistula plug will be associated with the plug-guiding device so as to be pushable along the plug-guiding device in the body.

In an additional aspect, the present invention provides a method of treating a fistula having at least a primary fistula opening in the alimentary canal, a secondary fistula opening, and a fistula tract extending therebetween. In this method, a plug-guiding device and a fistula plug delivery apparatus are provided. The plug-guiding device is configured to traverse the fistula tract and a portion of the alimentary canal. The fistula plug delivery apparatus is translatable along the plug-guiding device, and includes a fistula plug and a pushing element. The pushing element is effective to push the fistula plug through the alimentary canal. In one step, the plug-guiding device is positioned through the fistula tract and through a portion of the alimentary canal. In another step, the fistula plug delivery apparatus is associated with the plug-guiding device. The fistula plug delivery apparatus is then delivered along the plug-guiding device through the alimentary canal such that the pushing element pushes the fistula plug through the alimentary canal to the primary fistula opening. The fistula plug is then delivered along the plug-guiding device through the fistula tract toward the secondary fistula opening. The fistula plug delivery apparatus can be configured to translate along the plug-guiding device in any suitable manner. In some forms, the fistula plug, pushing element or both are receivable over the plug-guiding device for translation therealong. Additionally, the fistula plug may or may not be connected to the pushing element in the delivery arrangement. In some embodiments, the two are releasably connected to one another.

Other objects, embodiments, forms, features, advantages, aspects, and benefits of the present invention shall become apparent from the detailed description and drawings included herein.

BRIEF DESCRIPTION OF THE DRAWINGS

FIG. 9A is a partial, perspective view of a fistula plug useful in the present invention.

FIG. 9B is a partial view of the fistula plug of FIG. 10A, with the spreading wires spread apart and extending from the plug body lumen.

FIG. 9C is a partial view of the fistula plug of FIG. 10A, with the spreading wires collapsed and being pulled into the plug body lumen.

DETAILED DESCRIPTION

Figure 1:
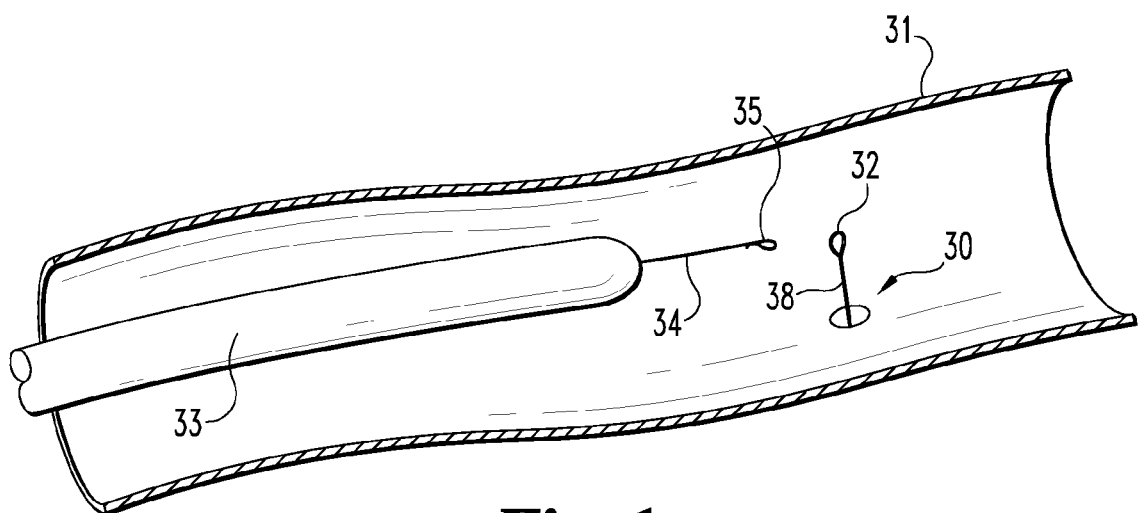
FIG. 1 is a partial view of fistula plug delivery system of the present invention, showing a plug-guiding device and a retrieving device delivered to an area in the alimentary canal near a primary fistula opening.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique methods and apparatuses for delivering fistula plugs into fistulae having at least a primary fistula opening, a secondary fistula opening, and a fistula tract extending therebetween. While some illustrative embodiments involve delivering a fistula plug into a fistula tract through a primary fistula opening and toward a secondary fistula opening, others involve delivering a fistula plug into a fistula tract through a secondary fistula opening and toward a primary fistula opening. Such methods and apparatuses may involve pushing and/or pulling a fistula plug through a fistula tract, potentially protected by a protective delivery device such as a sheath, capsule or other suitable delivery vehicle. In certain embodiments, and particularly some of those that involve directly or indirectly pushing a fistula plug through a body passageway, the fistula plug and/or a device (if present) being used to carry or otherwise deliver the plug will have sufficient column strength to be pushed through the passageway. In some aspects, a fistula plug is delivered into a fistula tract through a primary fistula opening and toward a secondary fistula opening while attached to or otherwise associated with a guidewire or other suitable plug-guiding device.

In some inventive methods, a fistula plug is delivered into a fistula tract utilizing a plug-guiding device (e.g., a guidewire) that does not travel from a secondary fistula opening to a primary fistula opening during the delivery procedure. Illustratively, such a method can involve positioning a plug-guiding device in a fistula tract by advancing the device through the tract from a primary fistula opening to a secondary fistula opening. Simultaneously (or in a subsequent step), a fistula plug associated with the plug-guiding device can be delivered into the fistula tract, for example, through the primary fistula opening and toward the secondary fistula opening. The association between the plug and the plug-guiding device may be such that the plug can be pushed along the plug-guiding device, pulled along and/or with the plug-guiding device, or both.

In one embodiment, such a method includes the provision of (i) a retrieving device having at least a distal portion; (ii) a plug-guiding device having at least a distal portion and a proximal portion; and (iii) a fistula plug. The retrieving device distal portion is advanced through the fistula tract from the secondary fistula opening to the primary fistula opening. The plug-guiding device distal portion is advanced through the alimentary canal and to the primary fistula opening, for example, while residing in an endoscope or other suitable endoluminally advancable device. Thereafter, the plug-guiding device distal portion is coupled to or otherwise suitably united with the retrieving device distal portion. While not necessary to broader aspects of the invention, in some embodiments, endoscopic or other visualization means will be provided at the treatment site to assist in uniting the two distal portions. Once the two distal portions are united, the retrieving device distal portion is withdrawn back through the fistula tract from the primary fistula opening to the secondary fistula opening, pulling the coupled plug-guiding device distal portion therealong to the secondary fistula opening. The fistula plug is associated with the plug-guiding device proximal portion, and delivered through the alimentary canal and into the fistula tract through the primary fistula opening while so associated. In accomplishing this delivery step, the fistula plug can be associated with the plug-guiding device in a variety of fashions including some that allow the plug to be pushed and/or pulled in the body. In some forms, a fistula plug, which is adapted for translation along a plug-guiding device, is associated with the plug-guiding device proximal portion, and thereafter, pushed and/or pulled along the plug-guiding device. Additionally or alternatively, the fistula plug can be directly or indirectly coupled to a plug-guiding device portion, and thereafter, pulled in the body, e.g., through the alimentary canal and/or into the fistula tract through the primary fistula opening.

With reference now to FIG. 1, shown are parts of one illustrative delivery system of the invention for delivering a fistula plug into a fistula tract. Extending through a primary fistula opening 30 occurring in a segment of an alimentary canal wall 31 is a distal portion of a retrieving wire 38. Although not necessary to broader aspects of the invention, in this specific illustrative embodiment, the distal portion of retrieving wire 38 includes a looped tip 32. As discussed elsewhere herein, other suitable looped and non-looped wire tips providing atraumatic surfaces for traveling through the body are contemplated as within the scope of the present invention. Such a retrieving wire distal portion may be passed through a secondary fistula opening (not shown in FIG. 1) and advanced through a fistula tract until it enters the alimentary canal through a primary fistula opening such as opening 30. There, it can be united with another part of the delivery system as described elsewhere herein. In embodiments where an endoscope or other visualization means is employed in a delivery procedure, any suitable step can be taken to enhance the visibility of a system component such as the distal portion of retrieving wire 38. These steps include but are not limited to making the distal portion radiopaque and/or brightly colored.

Examples of suitable loop tip wire guides can be found, for example, in pending U.S. application Ser. No. 11/234,992, filed Sep. 26, 2005, and entitled "LOOP TIP WIRE-GUIDE." While not necessary to broader aspects of the invention, in some instances, it may be desirable to employ a wire guide that is configured to be directable or steerable through the fistula tract or other body passageway. Examples of such devices can be found, for example, in pending U.S. application Ser. No. 11/234,990, filed Sep. 26, 2005, and entitled "STEERABLE LOOP TIP WIRE-GUIDE." These and other devices are particularly useful when treating gastro-cutaneous, entero-cutaneous, colo-cutaneous and other blind-ending fistulae, for example, wherein the distal end of a retrieving wire can be advanced through a fistula tract from a secondary fistula opening in the skin and toward a primary fistula opening at a subcutaneous location in the body.

Figure 2:
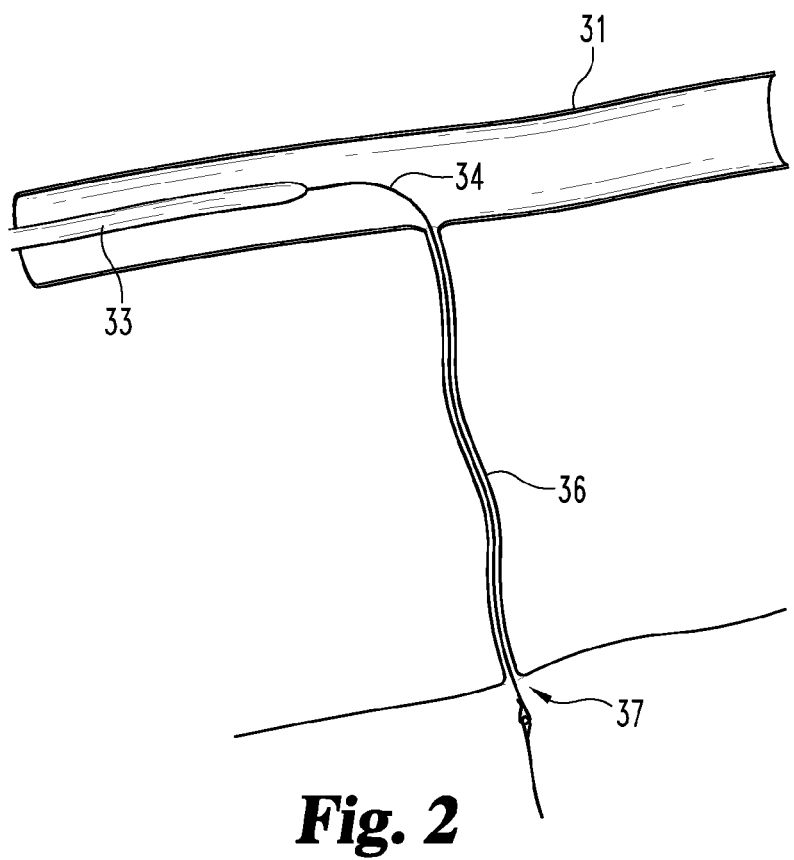
FIG. 2 shows the plug-guiding device of FIG. 1 united with the retrieving device of FIG. 1 and extending through a fistula tract from the primary fistula opening to a secondary fistula opening.

In addition to the looped-tip wire embodiment shown in FIG. 1, other suitable retrieving or retrievable devices are contemplated as within the scope of the present invention. For example, a retrieving device may be or include a catheter or other suitable endoluminally advancable device for traversing a fistula tract and providing means for uniting with a fistula plug-guiding device, for example, as shown in FIG. 2 and discussed in more detail below. In some cases, the retrieving device is comprised of a catheter in combination with a guidewire, wherein the catheter is effective to cannulate the fistula tract and/or infuse contrast media into the fistula tract. In this regard, a guiding catheter can be used to cannulate a fistula tract, and thereafter, a looped-tip or other suitable wire guide can be advanced through the emplaced catheter. The catheter can then be removed, leaving the wire in place and ready to be utilized for retrieval purposes or otherwise utilized as described herein. Alternatively, a device including a grasping or other capturing mechanism (e.g., a snare) can be advanced through an emplaced catheter, and then utilized to capture another part of a delivery system such as a plug, a plug-guiding device, a housing member, etc. The captured object may then be pulled into and through the catheter, or alternatively, the captured object and catheter can be pulled back and out of the tract simultaneously. In still yet another embodiment, a first wire guide can be used to cannulate a fistula tract, and thereafter, a guiding catheter can be advanced over the first wire and through the tract. Thereafter, the first wire can be replaced with a second wire capable of capturing or otherwise being joined to a plug or other delivery system component ready to be captured as described herein.

Continuing with FIG. 1, also shown is an endoscope 33 that has been advanced through the alimentary canal to a location near primary fistula opening 30. Extending from the distal end of scope 33 is a distal portion of an endoscopic wire 34. Although not necessary to broader aspects of the invention, in this specific illustrative embodiment, the distal end of wire 34 includes a capturing tip 35. In this regard, the endoscopist, while viewing the components through the endoscope, can manipulate wire 34 so that capturing tip 35 captures retrieving wire looped tip 32. Tip 35 includes a hook-shaped member wherein the distal end of wire 34 bends back over itself and touches or nearly touches another part of the wire, although a variety of other hook and non-hook capturing tips are contemplated as within the scope of the present invention.

A capturing tip, when incorporated into a wire or other device, can include any suitable adaptation to enable two or more objects to be connected to or to otherwise be united with one another. These include but are not limited to those involving single- and multiple-part coupling mechanisms, grasping devices including lockable and non-lockable forceps, magnetic devices (e.g., those employing rare earth magnets), clasps, various bonding materials effective to bond two objects (e.g., two wires) together, and combinations and variations thereof. In some forms, a tip provides an open hook or hook-like end, for example, one in the shape of a "shepherd's crook." In a preferred embodiment, endoscope 33 will include means for visualizing its advancement through the alimentary canal and identifying looped tip 32, primary opening 30, etc. As well, any of the devices described herein for traversing a passageway or other body opening (e.g., an alimentary canal, fistula tract, etc.) may be coated with or otherwise be comprised of a lubricious material to enhance its movement through the body.

The distal portion of a plug-guiding device such as wire 34 can be advanced through the alimentary canal to a location near a primary fistula opening in any suitable manner. In some cases, a guidewire itself will be advancable through the alimentary canal and potentially also into the fistula tract through a primary fistula opening. In preferred embodiments, a guidewire will be advanced while residing in an endoscope such as scope 33 or another suitable endoluminally advancable device known to those skilled in the art. These devices will generally have a lumen and include a "leading" distal end configured to at least pass through the alimentary canal. Nonetheless, it will be understood that such devices can exhibit any suitable size, shape and configuration for moving though the body as described herein. In some forms, the distal end of a device, or a portion thereof, will be particularly configured to avoid substantially cutting or tearing surrounding soft tissues or otherwise enhance its travel through body passageways. For example, a device distal end can include a tapered portion and/or have a dome-shaped or otherwise rounded tip.

Endoluminally advancable devices useful in the invention (e.g., guidewires, catheters, endoscopes, etc.) can be formed with one or more of a variety of materials. A particular material may be selected to take advantage of one or more of its properties such as but not limited to its weight, durability, flexibility, etc. For example, a device may comprise a material having properties that allow the device to traverse a body passageway without buckling or kinking or causing unacceptable damage to soft tissues defining the passageway. Illustratively, the device, or selected portions thereof (e.g., the distal end), can exhibit a degree of flexibility. In this regard, an endoluminally advancable device, or any portion thereof, may be rigid, malleable, semi-flexible, or flexible. In certain embodiments, an endoluminally advancable device is particularly adapted for moving through and into body passages that angulate sharply or curve abruptly such as when traversing the alimentary canal, passing through and into a fistula opening, traversing a fistula tract, etc. In some of these embodiments, the device is configured to be directable or steerable through the passageway, and therefore, exhibits desirable characteristics, e.g., sufficient stiffness, to allow an operator to apply an adequate degree of ante-grade force to the device to allow it to traverse a passageway in a desirable manner. In some forms, a device will be somewhat rigid in terms of column strength, yet will be equipped with one or more reliefs, indentations, thinner portions, or other similar adaptations along the device to provide some lateral flexibility to the device. Additionally or alternatively, a device may incorporate a mechanism of some sort that enables an operator to steer or otherwise navigate the device through a tortuous body passageway. These and other adaptations for facilitating advancement of a device through a body passageway will be recognized by those skilled in the art, and therefore, are encompassed by the present invention.

Suitable materials for forming these and other devices useful in the invention can include but are not limited to metallic materials including stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Additionally or alternatively, a device can include material in the form of yarns, fibers, and/or resins, e.g., monofilament yarns, high tenacity polyester, and the like. Devices can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon.

In some modes of operation, means for visualizing and/or irrigating a body passageway can be received within an endoluminally advancable device lumen. Illustratively, such means, as well as other desirable instruments and/or materials, can be passed into the proximal end of the device lumen (or alternatively, can be passed into one or more openings in a sidewall of the device), and through at least a portion of the device lumen. For example, in certain aspects, a device of the invention includes one or more ports in a sidewall thereof, wherein each port can be associated with a corresponding channel that extends from the port toward the distal end of the device. In some forms, one or more port and channel combinations are each configured to receive one or more instruments and/or materials therethrough. For example, a port can be configured to receive one or more optical fibers for visualization and/or illumination of a body passageway and surrounding soft tissues, for example, fiber-optic bundles including a plurality of glass fibers comprised of silicone, silicone dioxide, and/or a suitable equivalent. When used in the invention, these optical fibers are provided having suitable characteristics for the particular application including but not limited to suitable lengths and diameters, as well as degrees of flexibility or malleability.

Additionally, device ports can also be configured to receive fluids for the ante-grade irrigation of a body passageway. Such fluids can be provided from an external bag of fluid that is connected to the port of the irrigation channel by means of flexible tubing. If necessary, the fluid can be infused under pressure using a pressure bag applied to the fluid source, to increase the pressure under which the fluid is infused. Suitable device ports can further be configured to receive guidewires, drains, solutions such as sealants or sclerosants, high intensity light sources, a lever system to steer the device (e.g., wherein the device and/or its distal tip is directable in one, two, or three planes), and/or any other suitable instruments and/or materials. In some forms, a device port is configured to receive an optical viewing and lens system that may be attached to a video camera, a video monitor, and a video recorder for viewing at the distal end of the device.

Referring now to FIG. 2, once united with capturing tip 35, looped tip 32 can be pulled back through fistula tract 36 and out of the secondary fistula opening 37, thereby pulling the distal portion of endoscopic wire 34 therealong. Thereafter, scope 33 can be withdrawn back through the alimentary canal, and a fistula plug can be associated with a proximal portion (not shown) of endoscope wire 34. The fistula plug can then be advanced along this wire toward the primary opening, potentially residing in a protective housing or other delivery vehicle. Nonetheless, it will be understood that the order in which these steps (and steps of other inventive methods described herein) are carried out can be varied as desired to suit a particular application or situation. Accordingly, once looped tip 32 and capturing tip 35 are united, they can be kept at or near the primary opening while scope 33 is withdrawn back through the alimentary canal. Then, as the fistula plug is advanced along endoscope wire 34 toward the primary opening, it can be forced into the fistula tract over the point at which the two wires meet, or alternatively, the plug and the coupling point of the wires can be advanced into the fistula tract together with the coupling point residing at least partially inside or outside the plug.

These sorts of embodiments, i.e., those that involve bringing two endoluminally advanceable devices (e.g., guidewires) together at or near a primary fistula opening, and then maintaining the devices together (e.g., via a coupling mechanism) at this general location for at least part of the delivery procedure, are particularly advantageous when at least one of the devices provides a radiopaque tip. In this way, when another radiopaque object (e.g., a fistula plug, delivery device, etc.) is advanced toward the primary opening (e.g., along wire 34), it is possible to determine when this object is approaching the opening. Additionally, having a coupling point or other similar arrangement at or near the primary opening can provide a point of articulation at the primary opening so that the aggregate device does not have to make as acute a bend into the fistula tract. This may help to reduce trauma at the treatment site (e.g., to tissues adjacent the primary opening), as well as enhance the plug's ability to enter the tract.

In some modes, once retrieving wire 38 and endoscopic wire 34 are united at or near the primary opening, endoscopic wire 34 can be pulled back through scope 33 and out of the alimentary canal such that only retrieving wire 38 and scope 33 remain in the body. Scope 33 can then be removed from the body while holding the proximal end of retrieving wire 38 steady outside of the secondary fistula opening, leaving only the retrieving wire in the body. Retrieval wire 38 can then be utilized in an effort to push and/or pull a fistula plug through the alimentary canal. Illustratively, a fistula plug can be advanced along and/or with retrieval wire 38, through the primary opening, and into the fistula tract. It is also contemplated to simultaneously withdraw scope 33 and endoscopic wire 34 back through the alimentary canal with looped tip 32 and capturing tip 35 traveling inside or outside of the scope as it is withdrawn such that only retrieval wire 38 remains in the body.

In some embodiments, a plug-guiding device such as endoscope wire 34 can vary with regard to flexibility, stiffness, etc. along it length. Illustratively, wire 34 can have a more flexible distal portion relative to the remainder of the device to enhance travel of the distal portion through body passages having sharp bends, for example, through a tortuous fistula tract, into a fistula opening around a sharp bend, etc. A plug-guiding device can also include a stiffer proximal portion relative to the remainder of the device to enhance travel of the proximal portion through the alimentary canal. In some forms, wire 34 will have a preformed bend, curvature, etc. in the wire such that it assumes this shape upon removal from scope 33. Such a configuration can be helpful in guiding the distal end of the wire into the primary fistula opening in embodiments that involve this sort of maneuver, for example, where a wire from a scope is used to cannulate a fistula tract from a primary opening to a secondary opening.

Additionally, portions of a device such as endoscope wire 34 can include indicia (e.g., numbers, bands, dots or other scale-type markings) for use in measuring the length of a fistula tract. For example, when wire 34 includes such indicia, the indicia can be viewed by scope 33 at or near the primary opening when capturing tip 35 reaches the secondary fistula opening, thereby allowing the length of the fistula tract to be determined. A variety of other suitable ways in which to measure the length of a fistula tract will be recognized by the skilled artisan, and therefore, are encompassed by the present invention. Illustratively, the length of the tract could be determined by incorporating such indicia into retrieving wire 38, and then taking a measurement at the secondary opening when looped tip 32 reaches the primary opening to be viewed by the scope. Knowing the length of the fistula tract may advantageous in many respects including allowing the endoscopist to select a suitably sized plug, and to know where portions of a plug (e.g., a capping member) are positioned in relation to parts of the fistula (e.g., the primary opening) during delivery.

Figure 3:
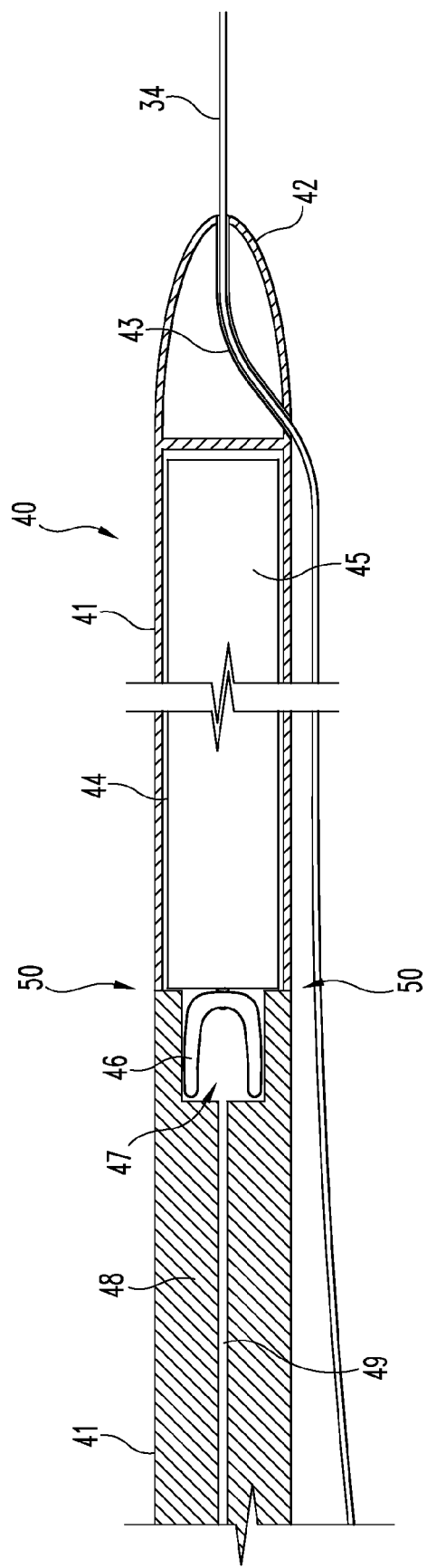
FIG. 3 shows a delivery device according to one embodiment of the present invention received over the plug-guiding device of FIG. 1.

Once a single-piece or multiple-piece plug-guiding device such as endoscopic wire 34 is located in the body such that it extends through the alimentary canal and through a fistula tract, a variety of fistula plugs and devices for carrying fistula plugs through the body can be associated with the plug-guiding device so that they can be advanced (e.g., pushed and/or pulled) through the alimentary canal and into the fistula tract through a primary fistula opening. With reference now to FIG. 3, shown is a fistula plug delivery device 40 according to one embodiment of the present invention. Device 40 is comprised of a delivery housing 41 having a distal portion 42. Delivery housing 41 may be formed with a synthetic polymeric material such as PTFE, although other suitable materials are contemplated as within the scope of the present invention. A wire channel 43 extends through distal portion 42 from a distal tip opening to a side opening, and is suitable for receiving endoscope wire 34 therethrough as shown. In this regard, delivery device 40 may be considered a "rapid exchange" or "short-wire" type, etc. delivery device, since endoscope wire 34 only passes through a relatively small segment of the device.

Delivery housing 41 also includes a plug body chamber 44 in which resides a fistula plug body 45. Plug body 45 can be formed with one or more of a variety of materials as discussed more thoroughly below. In some preferred embodiments, plug body 45 is comprised of a remodelable, angiogenic material such as a porcine small intestine submucosa. Attached to the proximal end of plug body 45 with a resorbable suture material (e.g., a 2-0 vicryl suture strand) is a compactable capping member 46. Such a capping member is optionally included, and in the current embodiment, includes a resilient wire frame supporting a deformable material covering (e.g., a naturally derived or non-naturally derived sheet-form material). As shown in FIG. 3, capping member 46 can be folded or otherwise compacted and positioned within capping member chamber 47, which is effective to maintain capping member 46 in a compacted condition until it is released from the chamber as described more thoroughly below in relation to FIG. 6. In this compacted condition, the resilient capping member 46 becomes a self-expanding device.

A wire channel, when incorporated into an over-the-wire object used in the invention (e.g., a fistula plug, plug housing, pusher, etc.), can be shaped and configured in a variety of manners, and can be routed through the object in a variety of ways. In some instances, a wire channel extending through a plug delivery housing will be somewhat longer than what is shown in FIG. 3. Illustratively, a wire channel can extend into a chamber that houses a plug body such that a guidewire could extend into this chamber and perhaps through a plug body residing in the chamber (e.g., through a central longitudinal lumen extending through the plug body along its length). Accordingly, in one embodiment that is otherwise similar to that shown in FIG. 3, the side opening of wire channel 43 is spaced relatively further from the distal tip of delivery housing 41 than what is shown in FIG. 3 (e.g., slightly proximal of capping member chamber 47). Fistula plug body 45 can then be constructed to have a central longitudinal lumen extending therethrough, and wire channel 43 can be routed into plug body chamber 44 such that endoscope wire 34 can be passed into delivery device 40 through the distal tip opening, into chamber 44, through fistula plug body 45, into chamber 47, through capping member 46, and out through the side opening.

In some forms, a plug body and/or a device being used in its delivery includes a radiopaque element such as but not limited to a radiopaque coating, attached radiopaque object, or integrated radiopaque substance for monitoring the movement of the object through the body during a delivery procedure. In this regard, any suitable radiopaque substance, including but not limited to, tantalum such as tantalum powder, can be incorporated into an inventive delivery device such as device 40 and/or any of its contents including fistula plug body 45 and capping member 46. Other radiopaque markers may be comprised of gold, bismuth, iodine, and barium, as well as other suitable radiopaque materials. In certain forms, a device components such as capping member 46 can be formed of a polymeric material loaded with a particulate radiopaque material.

Also forming part of delivery housing 41 is a pushing element 48, which is located proximal of plug body 45 in housing 41, and is effective to push delivery device 40 along endoscope wire 34 through the alimentary canal and into fistula tract 36 through primary opening 30. Pushing element 48 includes an optional lumen 49 extending therethrough along its length. Such a lumen may be used for flushing portions of the delivery device, hydrating a plug body and/or receiving a guidewire therethrough in an alternately configured delivery device, for example, in a "long-wire" style delivery device where a guidewire such as wire 34 passes through a substantial portion of the device (and potentially also through a fistula plug contained therein), or in an alternatively configured short-wire style device as described above. As well, there is a break point 50 at a location along delivery housing 41. Break point 50 is configured to enhance separation of housing 41 at this location when device 40 is suitably manipulated by an endoscopist or other operator, for example, as discussed more thoroughly below in relation to FIG. 6.

Figure 4:
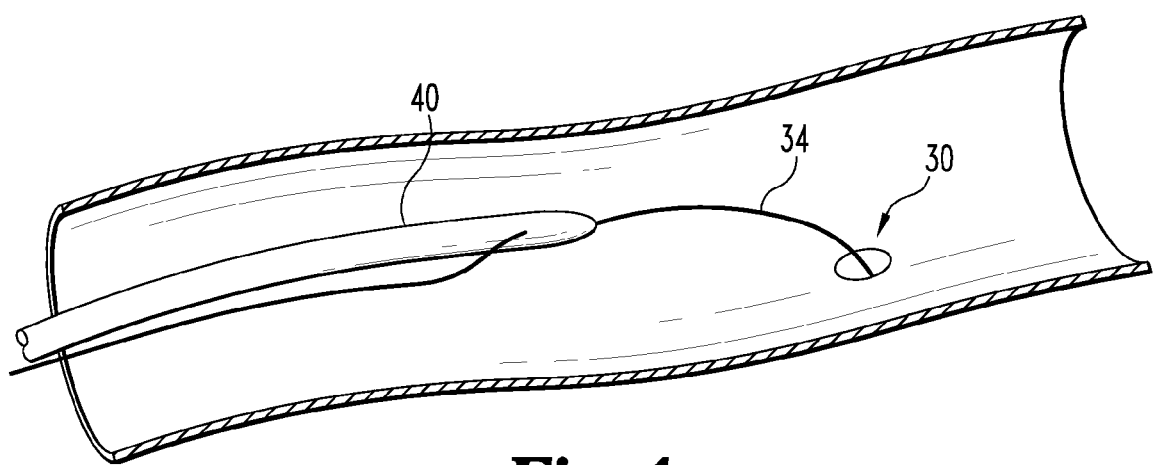
FIG. 4 shows the delivery device of FIG. 3 delivered to an area in the alimentary canal near the primary fistula opening.
Figure 5:
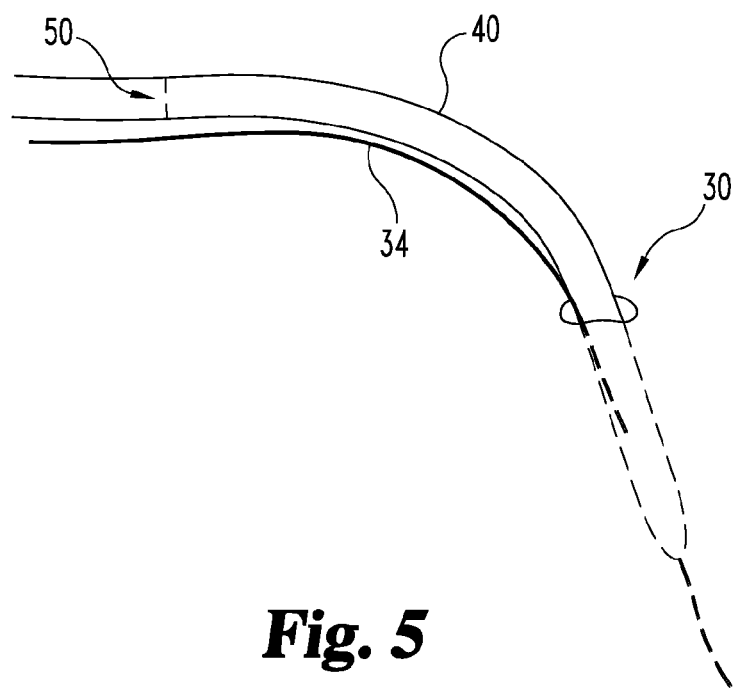
FIG. 5 shows the delivery device of FIG. 3 positioned in the fistula tract with a proximal portion of the device extending from the primary fistula opening.

After delivery device 40 is received over the proximal portion of endoscope wire 34, it can be advanced through the alimentary canal to a location near primary fistula opening 30 as shown in FIG. 4. Thereafter, delivery housing 41 can be further pushed along wire 34 until distal portion 42 enters fistula tract 36 through primary fistula opening 30 as depicted in FIG. 5. In an alternative embodiment, a delivery device is configured so that a fistula plug can be expelled from its distal end. Such a device can be received over the proximal portion of endoscope wire 34, and advanced through the alimentary canal to a location at or near primary fistula opening 30. Thereafter, a fistula plug body can be pushed and/or pulled from the distal end of the delivery device and into the fistula tract. Illustratively, a pusher that is translatable along (e.g., within) the delivery device can be incorporated and used to push the fistula plug out of the delivery device distal end. In some forms, the fistula plug will incorporate a collapsible-expandable capping member as described elsewhere herein, which can be collapsed for positioning in the delivery device. In this regard, as the plug body is pushed out of the delivery device, the capping member will eventually exit the device and expand for positioning at or near the primary opening. Alternatively, the plug body can be advanced into the fistula tract while residing in the delivery device. Then, with the collapsed and constrained capping member at or near the primary opening, the delivery device can be withdrawn back through the fistula tract, while holding the plug body steady (e.g., by applying counteraction with a pusher device), and until the capping member exits the delivery device distal end for deployment at or near the primary opening.

Although delivery device 40 in the current embodiment is pushed through the alimentary canal and into fistula tract 36 along wire 34, it will nevertheless be understood that certain other delivery devices in accordance with the invention are configured for travel through body passageways without tracking along a guidewire or other plug-guiding device. Illustratively, a delivery device can be configured so that it can be advanced through the alimentary canal in a manner similar to that described above for endoscope 33 (i.e., without tracking along a guidewire). Once at a location near a primary fistula opening, the device can then be coupled to a retrieving device and pulled into the primary opening with the retrieving device. In alternative embodiments, an inventive delivery system includes a steerable or otherwise self-directing delivery device (e.g., a scope, catheter, etc.) that can be advanced through the alimentary canal and into a fistula tract through a primary fistula opening without the aid of a retrieving device.

Figure 7:
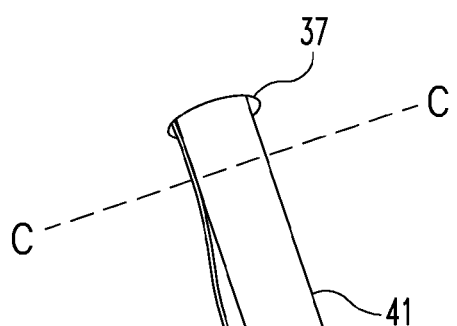
FIG. 7 shows a distal portion of the delivery device of FIG. 3 extending from the secondary fistula opening.

Referring now to FIG. 7, delivery housing 41 can be advanced through fistula tract 36 until distal portion 42 extends a distance out of secondary fistula opening 37. Thereafter, delivery housing 41 can be manipulated by an operator to cause delivery housing 41 to separate at break point 50. Break point 50 can be any adaptation along delivery housing 41 to allow one portion of the housing to separate from another portion of the housing upon sufficient manipulation by an operator (e.g., by grasping distal portion 42 and pulling, twisting, jerking, etc., while holding a proximal portion of delivery housing 41 steady). Illustratively, such a break point or other suitable body separation region can include one or more perforations, indentations, scores, thinner portions, etc. These and other adaptations for facilitating separation of portions of delivery housing 41 will be recognized by the skilled artisan and are therefore encompassed by the present invention. Additionally, delivery housing 41 can have some form of indicia (e.g., numbers, bands, dots or other scale-type markings) on its body to assist in determining how far one might want to extend the distal portion of delivery housing 41 out of secondary fistula opening 37. In this regard, indicia placed on a cannulating wire or catheter (e.g., retrieving wire 38) can be used to initially determine the length of the fistula tract. Thereafter, by having indicia on delivery housing 41 (e.g., starting at or near break point 50 and moving toward the distal end of the housing), the positioning of capping member 46 relative to the primary opening can be determined.

Figure 6:
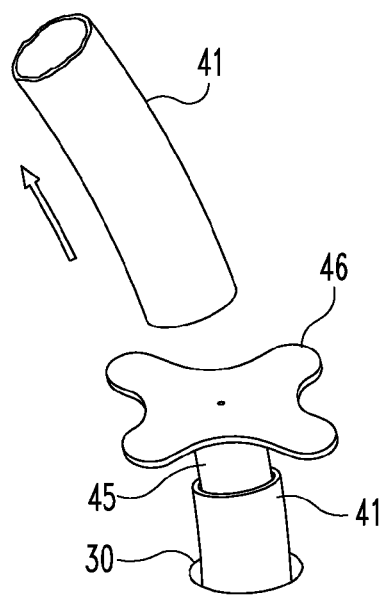
FIG. 6 shows the delivery device of FIG. 3 after the delivery housing has been separated at a break point along the housing to reveal a fistula plug therein.

Once delivery housing 41 is separated at break point 50, the housing segment that is proximal break point 50 can be withdrawn back through the alimentary canal, leaving the housing segment that is distal break point 50 in fistula tract 36. As these two segments move away from one another, expandable capping member 46 exits capping member chamber 47 and expands as shown in FIG. 6, i.e., so that the sides and bends of its resilient wire frame generally lie in a single, flat plane. While a preferred embodiment is four-pronged as shown, other non-polygonal and polygonal shapes can be used as well. The remaining (distal) segment of delivery housing 41 can then be pulled through fistula tract 36 until capping member 46 contacts portions of alimentary canal wall 31 adjacent to primary fistula opening 30. In preferred embodiments, fistula plug body 45 is attached to delivery device delivery housing 41 proximate the distal end of plug body 45 such that delivery housing 41 and fistula plug body 45 can generally move together when so pulled.

With capping member 46 desirably contacting portions of alimentary canal wall 31 adjacent to primary fistula opening 30, delivery housing 41 (and thus fistula plug body 45 contained therein) can be cut, for example, along cut line C-C shown in FIG. 7. These portions can then be removed and discarded, thereby exposing the newly-formed distal end of the fistula plug remaining in fistula tract 36. Any suitable device and/or technique may be used to perform this cut, with the cut occurring in any suitable location along delivery housing 41 (e.g., so that the newly-formed distal end of the fistula plug is flush with or extends a distance from or into secondary fistula opening 37 after the cut is made).

Figure 8:
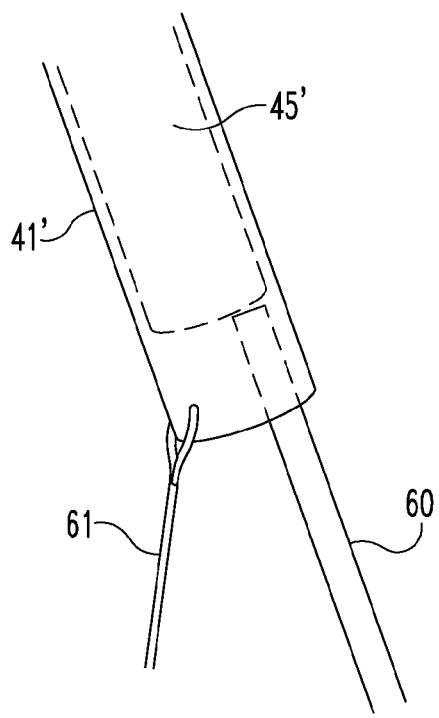
FIG. 8 shows the delivery device distal portion of FIG. 7 after it has been cut along cut line C-C shown in FIG. 7.

With reference now to FIG. 8, shown are the portions of delivery device delivery housing 41' and fistula plug body 45' remaining in fistula tract 36 after the above-described cut has been made. Pressure can be applied to the newly-formed distal end of plug body 45' with counteraction tool 60, while a grasping device 61 is used to grasp and pull the remaining portion of delivery housing 41' from fistula tract 36 through secondary fistula opening 37, leaving plug body 45' desirably positioned in fistula tract 36. In some cases, plug body 45' may need to be adjusted or otherwise manipulated after the remaining portion of delivery housing 41' has been removed. For example, plug body 45' can be hydrated if desired, and in some cases, plug body 45' will be secured (e.g., sutured) to portions of the patient's skin adjacent to secondary fistula opening 37 and/or a capping device applied to the newly-formed distal end of plug body 45'.

In some embodiments, the portion of delivery housing 41' remaining in the fistula tract includes an adaptation to facilitate its removal from the tract. Illustratively, a delivery housing such as delivery housing 41' can incorporate scores, thinner portions, and other openings and non-openings that weaken a portion of the housing to facilitate a splitting operation in removing the housing from the tract. Such a weakened portion may include any suitable means for facilitating tearing or breaking along the area. In certain beneficial forms, a protective sleeve or other delivery housing is controllably separable longitudinally into two or more pieces for removal, for example, as occurs in Peel-Away® catheters available from Cook Incorporated, Bloomington, Ind., USA. Such an apparatus with a separable sleeve is particularly useful in treating fistulae that have a secondary opening in the outer skin surface and a primary opening that is relatively difficult to access other than through the fistula tract, e.g. as occurs in a large percentage of enterocutaneous fistulae. These and other adaptations for facilitating removal of the delivery housing from the tract will be recognized by the skilled artisan and are encompassed by the present invention.

Fistula grafts suitable for use in the present invention such as fistula plug body 45 can exhibit a variety of shapes and sizes for delivery into a fistula tract. Generally, these grafts will be configured to extend through a fistula tract (or a segment thereof), and in some cases, will be sufficient to plug or otherwise fill at least a segment of the tract. In certain embodiments, a fistula graft will have a length of at least about 0.20 cm, and in many instances at least about 1 cm to about 20 cm (approximately 1 to 8 inches). In some cases, a fistula graft will have a length of from about 2 cm to about 5 cm, or alternatively, from about 2 inches to about 4 inches. Additionally, a fistula graft useful in the invention can have a diameter, which may or may not be constant along its length, from about 0.1 mm to about 25 mm, or more typically from about 5 mm to about 10 mm. In certain forms, a generally conical fistula plug is tapered along its length so that one end of the plug has a diameter of about 5 mm to about 10 mm, while the opposite end of the plug has a diameter of about 0.5 mm to about 3 mm. Such a taper may or may not be continuous along the length of the plug.

As well, fistula grafts useful in the present invention may be formed with one or more of a variety of materials. The materials used to form these grafts should generally be biocompatible, and in advantageous embodiments of the products, are comprised of a remodelable material. Particular advantage can be provided by fistula grafts including a remodelable collagenous material. Such remodelable collagenous materials, whether reconstituted or naturally-derived, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or within tissue in which a fistula graft of the invention is implanted, e.g., around tissue defining a fistula tract or an opening to a fistula.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Fistula grafts of the invention can include xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

ECM materials used in the invention may be essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Turning now to a discussion of drying techniques that can be useful in certain embodiments of the invention, drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. The amount of void space or open matrix structure within an ECM material that has been dried by evaporation is typically more diminished than, for example, an ECM material dried by lyophilization as described below.

A suitable lyophilization process can include providing an ECM material that contains a sufficient amount of hydrant such that the voids in the material matrix are filled with the hydrant. The hydrant can comprise any suitable hydrant known in the art, such as purified water or sterile saline, or any suitable combination thereof. Illustratively, the hydrated material can be placed in a freezer until the material and hydrant are substantially in a frozen or solid state. Thereafter, the frozen material and hydrant can be placed in a vacuum chamber and a vacuum initiated. Once at a sufficient vacuum, as is known in the art, the frozen hydrant will sublime from the material, thereby resulting in a dry remodelable material.

In alternative embodiments, a hydrated ECM material can be lyophilized without a separately performed pre-freezing step. In these embodiments, a strong vacuum can be applied to the hydrated material to result in rapid evaporative cooling which freezes the hydrant within the ECM material. Thereafter, the frozen hydrant can sublime from the material thereby drying the ECM material. Desirably, an ECM material that is dried via lyophilization maintains a substantial amount of the void space, or open matrix structure, that is characteristic of the harvested ECM material.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

In certain aspects, the invention provides fistula grafts including a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization.

Another method of dehydration bonding comprises pulling a vacuum on the assembly while simultaneously employing the vacuum to press the assembly together. Again, this method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Fistula grafts used in the invention may include biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Suitable biocompatible fistula grafts of the invention can also include a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly (ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

Fistula plug 45 and other suitable fistula grafts useful in the present invention can be prepared, for example, as described in International Patent Application Serial No. PCT/US2006/16748, filed Apr. 29, 2006, and entitled "VOLUMETRIC GRAFTS FOR TREATMENT OF FISTULAE AND RELATED METHODS AND SYSTEMS" (Cook Biotech Incorporated), which is hereby incorporated by reference in its entirety. In one embodiment, a fistula graft is comprised of a layered volumetric graft construct including, for example, a rolled remodelable material that occupies a substantially unitary volume. Illustratively, such a plug body can be formed by folding, rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, a plug member is formed by randomly or regularly packing one or more pieces of single or multilayer ECM sheet material within a mold and thereafter processing the packed material.

In some modes of operation, a hydrated graft material is provided within a single- or multiple-part mold having a plurality of apertures or holes extending through a wall of the mold, thereby providing access to the mold interior from an external location. These apertures can serve to enhance drying of a hydrated material during a processing step and in processes exerting vacuum pressure at these apertures, can promote and/or facilitate formation of surface protuberances on the graft material as portions of the same are drawn toward the apertures while under vacuum. In one aspect, an amount of ECM material is retained in such a mold, and needles or other material-displacing objects are inserted through some or all of the mold apertures and a distance into the ECM material, thereby displacing volumes of the ECM material. This can be performed when the graft material is hydrated, partially hydrated or dehydrated. In some forms, with needles inserted in a hydrated ECM material and providing passages therein, the material is subjected to conditions (e.g., freezing and/or dehydrating conditions) which, alone or in combination with one or more other conditions, cause or allow the passages to be generally retained in the ECM material after the needles are removed.

In another embodiment, a fistula graft comprises a compliant, biocompatible sheet-form material, for example, one or more layers of ECM material. Such a graft can be prepared, for example, as described in International Patent Application Serial No. PCT/US2006/16233, filed Apr. 29, 2006, and entitled "FISTULA GRAFT WITH DEFORMABLE SHEET-FORM MATERIAL" (Cook Biotech Incorporated), which is hereby incorporated by reference in its entirety. In one aspect, such a graft is sized and shaped so as to be deformable to a three-dimensional volumetric body extending through at least a segment of a fistula tract, and potentially filling at least a segment of the tract, the primary opening, and/or any secondary openings of the fistula. In so doing, advantageous implant materials will also be sufficiently flaccid to avoid substantial cutting or tearing of the surrounding soft tissues.

Capping members such as capping member 46, when utilized in present invention, can exhibit a variety of shapes, sizes and configurations. In general, a fistula graft including a capping member will be configured to have portions residing in and around a fistula opening, e.g., a primary fistula opening. For example, some fistula grafts useful in the invention include a biocompatible graft body which is configured to block at least the primary fistula opening, wherein the graft body includes a capping member and an elongate plug body, which extends from the capping member. The capping member is configured to contact portions of the alimentary canal wall adjacent to the primary opening, and the plug body is configured to extend into at least a portion of the fistula tract. In some instances, a capping member portion of a graft body will be effective to anchor or at least help anchor the graft body in the fistula tract. Advantageously, these capping member portions will be constructed so as to not cause undesirable damage to tissues adjacent the primary opening. In some forms, surfaces of a capping member that will come into contact with tissues at a treatment site will be formed with softer, more compliant materials and/or will be specially contoured (e.g., rounded) to promote desirable contact with these tissues. Certain capping members will be designed to reduce and/or more evenly distribute pressure placed on tissues adjacent the primary opening by the capping member.

A capping member and an elongate plug member may be formed separately and then attached to one another or otherwise suitably united, or alternatively, the two may be formed as a single unit, for example, from a single piece of material or other object. When formed separately, a capping member and an elongate plug member may be united, for example, using an adhesive, by suturing, using mechanical fastener(s), and/or employing any other suitable joining means. Additionally, a capping member and an elongate plug member may be formed with one or more of a variety of suitable biocompatible materials. In some forms, the graft body is configured to seal off or substantially seal off the primary fistula opening when suitably deployed.

A capping member can include one or more objects (e.g., devices, pieces of material, etc.) that, together or alone, exhibit a three-dimensional rectilinear or curvilinear shape. Suitable three-dimensional rectilinear shapes can have any suitable number of sides, and can include, for example, cubes, cuboids, tetrahedrons, prisms, pyramids, wedges, and variations thereof. Suitable three-dimensional curvilinear bodies can include, for example, spheres, spheroids, ellipsoids, cylinders, cones, and any suitable variations thereof (e.g., a segment of a sphere, or a truncated cone, etc.). Capping members and capped plugs useful in the invention can be prepared, for example, as described in International Patent Application Serial No. PCT/US2006/024260, filed Jun. 21, 2006, and entitled "IMPLANTABLE GRAFT TO CLOSE A FISTULA" (Cook Biotech Incorporated); and International Patent Application Serial No. PCT/US2007/61371, filed Jan. 31, 2007, and entitled "FISTULA GRAFTS AND RELATED METHODS AND SYSTEMS FOR TREATING FISTULAE" (Cook Biotech Incorporated), which are hereby incorporated by reference in their entirety. In some aspects, a fistula plug includes more than one capping member, for example, a capping member to be positioned at a primary fistula opening and a capping member to be positioned at a secondary fistula opening. In preferred aspects, a capping member and/or a plug body comprise a remodelable, angiogenic material, for example, a remodelable extracellular matrix material such as submucosa.

Figure 12:
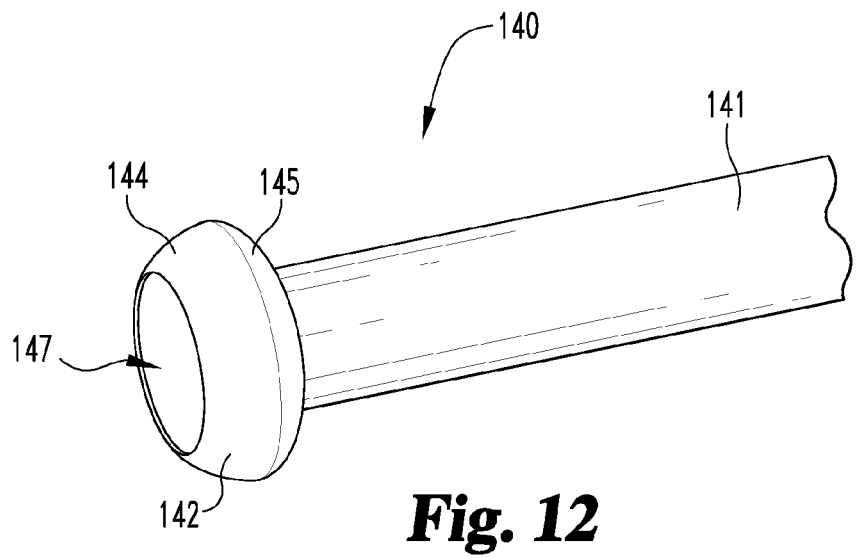
FIG. 12 is a partial view of a fistula plug according to another embodiment of the present invention.

In embodiments of the invention involving delivery of such grafts, the graft (or any portion thereof including a capping member) can be configured to reside within a delivery vehicle during a delivery step, although embodiments where no part of a graft resides within a delivery vehicle during delivery are contemplated as well. With reference now to FIG. 12, shown is a fistula plug 140 according to another aspect of the invention. Plug 140 includes an elongate plug body 141 and a capping member 142. Capping member 142 has a first end 144 and a second end 145, wherein the elongate plug body extends from capping member second end 145. Capping member first end 144 and second end 145 each provide rounded, tapering surfaces extending from a middle region of the member. Capping member 142 is formed with a synthetic polymer, and includes an optional hollow portion that extends at least partially through the member. While not necessary to broader aspects of the invention, in some embodiments, the elongate plug body will extend into this hollow portion. The rounded, tapering contour of capping member second end 145 can enhance the contact of the capping member with patient tissues adjacent the primary fistula opening, for example, by allowing a more even distribution of pressure to be applied by the capping member to these tissues and/or otherwise reducing irritation or other trauma caused to these tissues. A variety of capping member shapes and configurations may be useful in this regard including some of the collapsible and non-collapsible capping members described elsewhere herein. In some forms, suitable capping members will be provided by a PEG bolster device or another similar device that is known for attachment to PEG tubes, for example, to enhance the relationship between the tube and surrounding tissues.

In use, fistula plug 140 can be advanced through the alimentary canal and into a fistula tract through a primary opening according to any of the delivery methods described herein, potentially with all or part of the plug residing in a protective housing or other delivery vehicle. Accordingly, plug 140 can be pushed and/or pulled through the body. In a preferred embodiment, the maximum diameter of capping member 142, while permitting the capping member to pass freely through the alimentary canal, is greater than the general diameter of the primary fistula opening such that plug body 141 can be advanced through the primary opening and through the fistula tract toward a secondary fistula opening until capping member 142 prevents plug 140 from being further advanced. Thereafter, plug 140 can be fixed or otherwise held in this location, for example, by suturing the plug to patient tissue at the secondary opening, etc. When seated at the primary opening, the capping member can enhance the plugging arrangement in a variety of ways including but not limited to by anchoring the plug body, protecting the plug body, blocking the primary fistula opening and/or improving the manner in which the plug interacts with surrounding tissues. Additionally, in some forms, the capping member will be attached directly to the plug body, for example, with a resorbable suture or other degradable coupling device.

In this regard, in embodiments of the invention where a plug body and a capping member are formed as separate constructs, the two may be coupled to one another with an absorbable coupling device or material. These coupling elements can exhibit any suitable size, shape, and configuration, and in some aspects, take the form of an adhesive or one or more hooks, fasteners, barbs, straps, suture strands, or combinations thereof. Also, such coupling elements may be comprised of one or more of a variety of suitable biocompatible materials exhibiting a rate of degradation upon implantation in vivo, such as but not limited to a 2-0 vicryl suture material. Illustratively, a coupling element can be adapted to desirably hold a capping member and plug body in association with another during product handling and implantation, and then upon implantation, to degrade at a desirable rate. In some modes of operation, the capping member and plug body, at least due in part to degradation of the coupling element, can uncouple or otherwise disengage from one another after a period of time following implantation, allowing the capping member to be discarded, e.g., to pass through and out of the bowel with naturally occurring fecal mater. In some instances, such decoupling can be facilitated and/or promoted by naturally occurring forces generated during peristalsis.

While a non-collapsible capping member such as that shown in FIG. 12 may be useful in some instances, a capping member can also comprise an expandable element, for example, an expandable material such as a compressed sponge material and/or an expandable device such as a resilient wire frame. In some embodiments, a capping member includes a support frame that is constructed using one or more pieces of stainless steel wire, superelastic wire or any of a variety of other suitable materials described herein or otherwise known to those skilled in the art. Illustratively, a support frame can include a single piece of Nitinol wire having a plurality of sides and bends interconnecting adjacent sides. The bends can be coils, fillets, or other configurations to reduce stress and fatigue. The single piece of wire can be joined by an attachment mechanism, such as a piece of cannula and solder, to form a closed circumference frame.

Expandable capping members, when used in the invention, include those that are self-expanding, as well as those that require at least some manipulation in order to expand. An expandable capping member can be allowed to expand, for example, upon removal from a chamber or other open space in a delivery device, or when another object being used to constrain the capping member (e.g., a suture, guidewire, trigger wire, etc.) is removed, released, actuated, etc. In some forms, a capping member is releasably maintained in a compacted condition by an elongate element (e.g., a suture, a guidewire, etc.) that passes through and/or alongside the capping member.

Figure 11A:
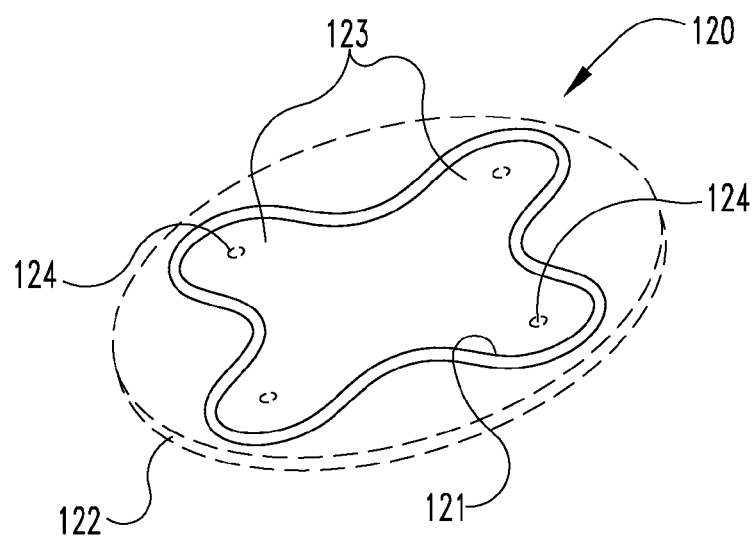
FIG. 11A shows a capping member according to one embodiment of the present invention.

With reference now to FIG. 11A, shown is a capping member 120 according to another embodiment of the present invention. Capping member 120 includes a resilient support frame 121 supporting a deformable covering material 122 (shown in phantom). In this specific illustrative embodiment, support frame 121 is shaped such that when it is lying in a single, generally flat plane as shown in FIG. 11A, it provides a plurality of lobes 123 extending away from a central region of the frame. As shown, an aperture 124 extends through covering material 122 at a location near the apex of each of the lobes, to the interior side of the frame. With support frame being flexible and resilient, lobes 123 can be moved toward one another to generally align apertures 124 such that a wire guide or other elongate element can be passed through the apertures for maintaining the lobes in a compacted or otherwise lower profile condition for traversing parts of the body (e.g., the alimentary canal, a fistula tract, etc.) and/or for fitting in a delivery device lumen.

Figure 11B:
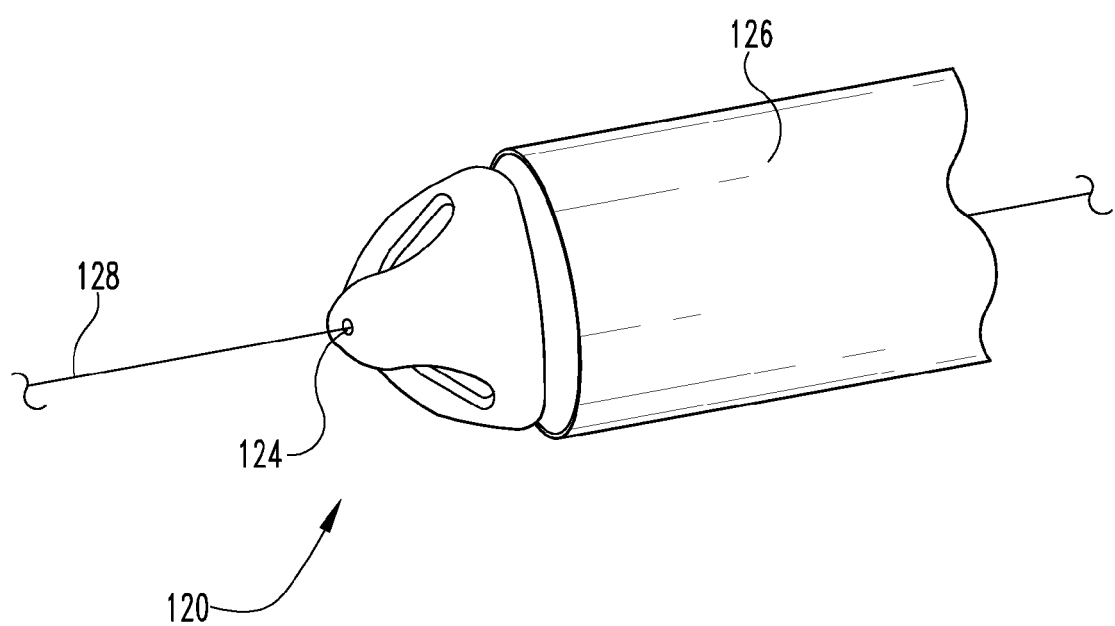
FIG. 11B shows a partial view of an inventive fistula plug incorporating the capping member of FIG. 11A.

Referring now to FIG. 11B, shown is a partial view of an inventive fistula plug incorporating capping member 120. While capping member 120 could be utilized in a variety of the inventive devices and apparatuses described herein, in this specific illustrative embodiment, it is coupled to a generally cylindrical plug body 126. Plug body 126 provides a central longitudinal lumen through which a guidewire 128 can be passed, and in this regard, guidewire 128 can be passed through the plug body lumen, through a center hole in capping member 120, and through each of apertures 124, thereby keeping capping member 120 releasably constrained in a relatively lower profile condition as shown.

While not necessary to broader aspects of the invention, inventive plugs having the sort of capping arrangement shown in FIG. 11B are particularly useful in embodiments where the plug is configured to travel in the body without residing in a delivery housing or other delivery vehicle. In this regard, an inventive plug such as that shown in FIG. 11B could be advanced along guidewire 128 according to any of the methods and techniques described herein (e.g., utilizing a pushing element and/or pulling element) until it reaches a fistula treatment site. When this sort of plug is to be pushed through the body, a pushing element, which is particularly configured so as to not undesirably contact and interfere with capping member 120 in its constrained condition, may be employed. Such a pushing element can have portions that extend around and/or through capping member 120 in its constrained condition so as to not make undesirable contact. Additionally or alternatively, plug body 126 can have a portion that extends back through the capping member and provides a surface that a pusher or other pushing element can contact for pushing the plug through the body. In some instances, this additional plug body portion will not be attached to the remainder of the plug body so that the additional portion can fall away and be carried out of the body after the deployment procedure is completed.

Once capping member 120 is desirably positioned at or near a primary fistula opening, guidewire 128 can then be removed to enable capping member 120 to return generally to its unconstrained condition for placement at the primary opening. In an alternative embodiment, capping member 120 is similarly held by a wire (e.g., a "trigger" wire) or other elongate element, which extends along (e.g., through) plug body 126 to hold capping member 120 in a releasably constrained condition, but which unlike guidewire 128 is not also used as a means for guiding plug body 126 through the body. Once capping member 120 is desirably located in the body, such an element can then be manipulated (e.g., pulled, twisted, etc.) to release capping member 120 from its constrained condition.

A capping member frame can comprise a metallic material including but not limited to stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Additionally or alternatively, suitable frames can include material in the form of yarns, fibers, and/or resins, e.g., monofilament yarns, high tenacity polyester, and the like. A frame element can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon. Such metallic and other materials may be used in forming other expandable and non-expandable fistula graft components useful in the present invention. Capping member 46 also includes a flexible material covering extending between sides of the frame. Such a covering can be formed with any suitable material such as but not limited to DACRON, PTFE, collagen, submucosa, and other flexible materials, and can be attached to the frame with sutures or other suitable attachment means.

In some embodiments, a capping member includes a support frame and a deformable covering material. The support frame and covering material can each be formed with one or more of a variety of materials. Illustratively, a support frame that is made of a resilient material (e.g., Nitinol) may be combined with a naturally derived or non-naturally derived sheet-form material, wherein this combination provides a suitable arrangement for blocking, and in some cases sealing off, a fistula opening. In some preferred embodiments, the deformable material is comprised of a polymeric material, e.g., a synthetic polymeric material such as but not limited to polyurethane materials such as THORALON®, thermoplastic silicones, etc. In some instances, a naturally-derived material such as an ECM or other naturally-derived material is additionally or alternatively included. Such materials may be coated with other material(s), for example, a PCL-coated or PLGA-coated collagenous material (e.g., a coated SIS material). Such materials may be fully or partially formed on and/or around a support frame, or alternatively, may be provided as a separate component and then suitably combined with the support frame. In a preferred embodiment, a synthetic polymer is desirably thermoformed around a support frame to fully or partially embed parts of the support frame. Some of these devices can be used to treat fistulae having a primary opening in a bowel wall, and in this regard, may be effective to block or otherwise exclude the bowel lumen from the fistula tract when desirably deployed.

Referring now to FIG. 9A, shown is another fistula plug 80 that can be used in the present invention. Fistula plug 80 includes a generally cylindrical plug body 81 having a central lumen 82 extending therethrough along its length. Fistula plug 80 also includes a capping member 83, which is coupled to one end of plug body 81 with resorbable suture material. Capping member 83 is generally in the shape of a disc having an outer, annular portion 84 and four spoke-like portions 85 extending inward from annular portion 84. Each capping member spoke-like portion 85 has a channel 86 defined therein into which a frame or frame-like component can be received.

In the current embodiment, fistula plug 80 includes a removable frame component 88, which is comprised of four resilient wires 89 extending from a main pulling wire 90. Wires 89 may be associated with pulling wire 90 in any suitable manner (e.g., attached to the pulling wire, converging into the pulling wire, etc.), and are configured to spread away from one another when not constrained or not sufficiently constrained. Capping member 83 may be formed with any suitable material, and in advantageous embodiments, will be formed with a somewhat flexible material to allow the member to be folded or otherwise collapsed and positioned in a delivery device lumen in which fistula plug 80 is housed. In this regard, each of wires 89 can be positioned in a respective channel 86, and when flexible capping member 83 is collapsed, the wires can also be collapsed. Then, when capping member 83 is removed from the delivery device lumen (or otherwise presented in an unconstrained state), wires 89 are effective to unfold capping member 83 as shown in FIG. 9A as they spread away from one another. Frame component 88 can then be removed and discarded as described below, or alternatively, it can remain in the plug after the plug is deployed. It will be understood that other suitable removable frame component and capping member configurations and arrangements will be recognized by those skilled in the art and are encompassed by the present invention.

FIG. 9B shows wires 89 in an unconstrained state and extending from plug body lumen 82. When pull wire 90 is pulled in the direction of the arrow as shown in FIG. 9C, wires 89 are forced toward one another as they are pulled into narrow plug body lumen 82 and toward the other end of plug body 81. While FIGS. 9B and 9C exclude capping member 83 for simplicity reasons, it will nevertheless be understood that fistula plug 80 can be constructed without capping member 83. In some aspects, such a plug includes a resorbable frame component similar to component 88 that is configured to remain in the patient after the plug is deployed, for example, to provide a capping member for anchoring or other purposes.

Fistula plug 80 can be delivered into a fistula tract in a variety of manners so that capping member 83 is placed at a primary opening. Illustratively, some methods involve advancing the plug through a fistula tract from a primary fistula opening and toward a secondary fistula opening. In one embodiment, plug 80 is positioned in a delivery device, and advanced through the fistula tract along a plug-guiding device, e.g., as shown in FIG. 5. Alternatively, delivery of plug 80 can involve advancing the plug through a fistula tract from a secondary fistula opening and toward a primary fistula opening. In one embodiment, a plug such as plug 80 is delivered using a delivery device having a lumen communicating with a distal end opening. Illustratively, plug 80 can be placed in the delivery device lumen with capping member 83 near the distal end opening. The delivery device can then be advanced through the fistula tract until the capping member passes through the primary opening and into the alimentary canal. Thereafter, capping member 83 can be removed from the delivery device lumen (e.g., by holding the plug in place and withdrawing the delivery device), allowing wires 89 to spread apart and unfold the capping member in the alimentary canal. If necessary, plug 80 can be pulled back until capping member 83 contacts portions of the alimentary canal wall adjacent to the primary opening. Pulling wire 90 can then be used to pull wires 89 out of channels 86, leaving capping member 83 deployed in the body. In some forms, pulling wire 90 resides within plug body 81, and a portion of body 81 extending from the secondary opening (i.e., opposite capping member 83) can be cut off to expose wire 90. The portion of the plug body remaining in the patient can then be held in place, while pulling wire 90 is used remove frame component 88 from the plug.

As disclosed above, the present invention also provides, in certain aspects, methods and apparatuses for delivering a fistula plug into a fistula tract, which involve pushing and pulling the fistula plug through the fistula tract from a first fistula opening toward a second fistula opening. In one embodiment, the invention provides a fistula plug delivery system including a delivery apparatus and a fistula plug translatable along the delivery apparatus. The delivery apparatus is configured to traverse the fistula tract, and includes a pushing element and a pulling element. The pushing element and the pulling element are effective to advance the fistula plug through the fistula tract from the first fistula opening toward the second fistula opening. Use of such a system can include positioning the delivery apparatus in the fistula tract, and associating the fistula plug with the delivery apparatus, wherein the pushing element contacts the fistula plug in a first location, and the pulling element is coupled to the fistula plug at a second location spaced from the first location. The fistula plug is then delivered into the fistula tract along the delivery apparatus, wherein the fistula plug is advanced through the fistula tract from the first fistula opening toward the second fistula opening with the pushing element and the pulling element. In some embodiments, the pushing element and/or the pulling element do not contact the fistula plug directly, but rather contact a delivery vehicle (e.g., a capsule, sheath, catheter, etc.) in which the plug resides, for example, with the pushing element contacting the delivery vehicle in a first location, and the pulling element being coupled to the delivery vehicle at a second location spaced from the first location. These and other apparatuses and methods of the invention are particularly useful in treating gastro-cutaneous, entero-cutaneous, colo-cutaneous and other blind-ending fistulae.

Figure 10:
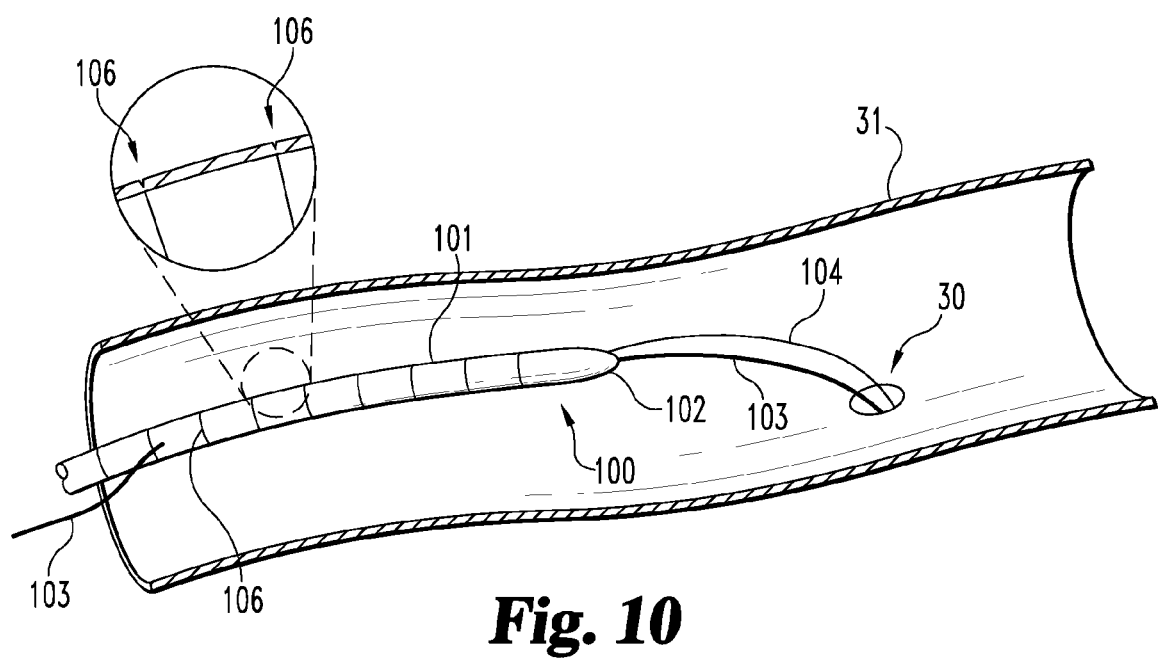
FIG. 10 shows another delivery device of the present invention delivered to an area in the alimentary canal near a primary fistula opening.

FIG. 10 shows another fistula plug delivery device 100 of the present invention at a location in the alimentary canal near primary fistula opening 30. Device 100 is comprised of a delivery housing 101, which has a distal portion 102 and is configured to house at least one fistula plug. Delivery housing 101 may be formed with any suitable material such as a synthetic polymeric material. Device 100 is received over a guidewire 103, which extends through the alimentary canal and through a fistula tract from primary fistula opening 30 to a secondary fistula opening (not shown). A pulling wire 104 extends from distal portion 102 into the fistula tract through primary fistula opening 30. Pulling wire 104 can be coupled to or otherwise associated with device 100 in any suitable manner including but not limited to those that involve tying, bonding, welding, and using a pin vise-like mechanism and/or other single-part or multiple-part coupling mechanisms. Pulling wire 104 is effective to pull delivery device 30 along guidewire 103 through the alimentary canal and potentially also into the fistula tract through primary fistula opening 30. Also forming part of delivery device 100 (but not shown) is a pushing element, which is effective to push delivery device 100 along guidewire 103 through the alimentary canal and potentially also into the fistula tract through primary fistula opening 30. Any of the pushing elements described herein may be utilized in this regard. Illustratively, the delivery device may directly or indirectly incorporate the pushing element, for example, as is shown in FIG. 3, or alternatively, the pushing element may be a separate component also configured for advancement along guidewire 103.

Guidewire 103 and pulling wire 104 can be delivered into position in any suitable manner to provide the type of arrangement shown in FIG. 10. In one embodiment, the distal end of a retrieving wire such as that shown in FIG. 1 is passed through a secondary fistula opening and advanced through a fistula tract until it enters the alimentary canal through a primary fistula opening such as opening 30. An endoscope such as that shown in FIG. 1 is advanced through the alimentary canal to a location near primary fistula opening 30. This scope can house or otherwise provide wires 103 and 104 such that the distal end of each wire (e.g., each comprised of a capturing tip) can be extended from the distal end of the scope and manipulated by the endoscopist to capture or otherwise be joined to the distal portion of the retrieving wire.

Once united with wires 103 and 104, the retrieving wire is pulled back through the fistula tract and out of the secondary fistula opening, thereby pulling the distal portions of guidewire 103 and pulling wire 104 therealong. Thereafter, the scope is withdrawn back through the alimentary canal, and fistula plug delivery device 100 (with pulling wire 104 attached to the distal end 102 thereof) is received over the proximal portion (not shown) of guidewire 103 and advanced to a location near primary fistula opening 30. In an alternative form, only one of wires 103 and 104 provides means for capturing or otherwise uniting with the retrieving wire), and the wire without this means is attached to or otherwise associated with this wire so as to be carried along therewith. Still other modes are contemplated for providing the type of wire arrangement shown in FIG. 10. Illustratively, a pair of retrieving wires can be passed through a secondary fistula opening and advanced through a fistula tract until it enters the alimentary canal through a primary fistula opening such as opening 30. Additionally, a wire, catheter, etc. can be advanced through the alimentary canal to a location near primary fistula opening 30. Thereafter, this wire, catheter, etc. can be directly or indirectly united with both wires and pulled back through the alimentary canal, thereby pulling the two wires therealong. With both wires extending through the alimentary canal and the fistula tract, a fistula plug (potentially housed in a delivery vehicle) can be associated with the two wires at the ends of the wires extending from the alimentary canal. In this regard, one wire may be utilized in an effort to pull the fistula plug through the body (e.g., by coupling to the fistula plug distal end), and the other wire may be utilized in an effort to push the fistula plug through the body (e.g., by receiving all or part of the plug over the second wire and using a pushing element to push the plug along the second wire).

Continuing with FIG. 10, a plurality of articulation adaptations 106 occur along delivery housing 101. These sort of adaptations may occur along all or a portion (e.g., a distal portion) of a delivery housing such as housing 101. Such adaptations can enhance the travel of delivery housing 101 through body passages, particularly when negotiation around sharp bends is required, e.g., around a sharp bend entering a primary fistula opening from the alimentary canal. In some forms, a delivery housing will be somewhat rigid in terms of column strength, yet will be equipped with one or more reliefs, indentations, thinner portions, or other similar adaptations along the housing to provide some lateral flexibility to the housing. These and other adaptations for enhancing articulation of delivery housing 101 will be recognized by the skilled artisan and are encompassed by the present invention. Additionally or alternatively, one or more articulation adaptations such as those described above can be incorporated into the body of a fistula plug used in the invention. Illustratively, circumferential cuts may be made in outer layers of a rolled, sheet-form collagenous construct. Such articulation adaptations may be advantageous in instances where a plug has to make an acute bend, for example, when passing into a fistula tract. While not necessary to broader aspects of the invention, in certain aspects, plugs of this sort may be delivered into a fistula tract while not residing in a delivery housing or other protective member.

In some embodiments, a fistula plug is configured for advancement through the body, e.g., along a guidewire or other plug-guiding device, etc., while not residing in a delivery housing or other delivery vehicle. These and other plug bodies useful in the invention may be equipped with a hydration resistant component incorporated on or in the plug body. Illustratively, a hydratable plug body that may potentially come into contact with bodily or other fluids during delivery may include a hydration resistant coating material (e.g., a degradable material) that coats a surface of the plug body. A variety of other ways to alter the hydration resistance of a plug body material will be recognized by those skilled in the art, and therefore, are encompassed by the present invention. These include but are not limited to increasing the density of a porous plug body material, and then stabilizing the material in this higher density state. Additionally or alternatively, a variety of hydrophobic materials including various hydrophobic polymers, waxes and oils can be incorporated into a plug body.

Figure 13:
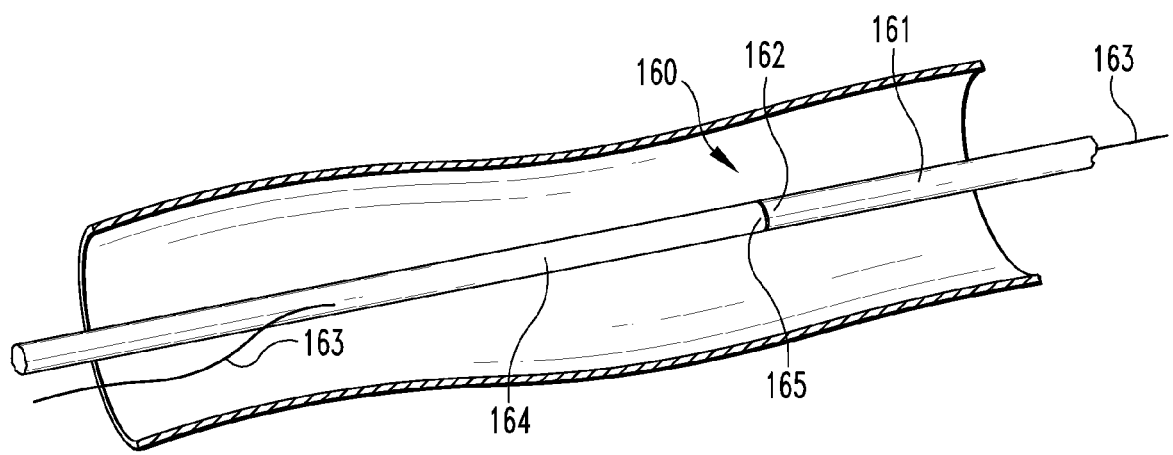
FIG. 13 depicts a step of one illustrative inventive method and components of inventive devices and apparatuses.

FIG. 13 shows parts of another fistula plug delivery system 160 of the present invention at a location in the alimentary canal. System 160 is comprised of a fistula plug 161 having a proximal portion 162. In this specific illustrative embodiments, plug 162 is formed with a collagen-containing material and exhibits a generally cylindrical shape, although any of the fistula plugs described herein including those housed in a delivery housing, sheath, etc. and those additionally or alternatively providing some sort of capping arrangement, etc. could be utilized in this regard. Fistula plug 162 is received over an emplaced guidewire 163, which extends through the alimentary canal and potentially also through a fistula tract from a primary fistula opening to a secondary fistula opening. Guidewire 163 can be delivered into position in any suitable manner including those described herein to provide the type of arrangement shown in FIG. 13.

Also forming part of delivery system 160 is a pushing element 164 having a distal end 165. When received over guidewire 163 as shown in FIG. 13, the distal end of the pushing element can contact the proximal end of the fistula plug, and in this regard, pushing element 164 can be used to push fistula plug 161 along the guidewire through the alimentary canal and potentially also into a fistula tract through a primary fistula opening. Guidewire 163 extends through pushing element 164 in a wire channel having a first opening in the distal end of the pushing element and a second, side opening spaced a distance from the distal end opening. Since the distance between the two openings is relatively short, pushing element 164 may be positioned over the guidewire more quickly compared to a pushing element having a longer wire channel or one that is configured to be entirely received over a guidewire.

A passage or other open space (e.g., a channel) in a pushing element for receipt of a guidewire can be shaped and configured in a variety of manners, and can be routed through the pushing element in a variety of ways. Accordingly, a wire channel can be somewhat longer or shorter than what is shown in FIG. 13. In some instances, a longitudinal slit, crevice, slot or other opening in a side wall of a pushing element (e.g., a longitudinal slit extending a distance from a distal end of a pusher, and communicating with a central longitudinal lumen of the pusher), provides a suitable space through which a guidewire or other plug-guiding device can be passed. This types of configuration allows for a guidewire to be fed into and stripped out of the pusher from the side.

In one embodiment, a pusher similar to that shown in FIG. 13 additionally includes a longitudinal side wall opening (e.g., a slit) communicating with an inner lumen, and extending from a point just proximal of the wire channel side opening to the proximal end of the pusher. With this type of configuration, a guidewire exiting the pusher through the wire channel side opening can be passed back into the pusher though this longitudinal side wall opening so that the guidewire can extend proximally along the pusher in the inner lumen of the pusher. Thus, while FIG. 13 shows guidewire 163 exiting the wire channel side opening and extending through the alimentary canal alongside the pusher, in other forms, the pusher will be adapted as described above so that the guidewire can be fed back into the pusher for traversing the alimentary canal. Illustratively, with a sufficient length of wire extending from the alimentary canal, the plug can be received over the wireguide by feeding the wire through the wire channel. Wire exiting the wire channel side opening can then be fed into the longitudinal side wall opening, for example, as the pusher is being advanced into the alimentary canal over the emplaced guidewire. In this way, the guidewire can travel inside the pusher while traversing the alimentary canal. When desired, the guidewire can then be stripped back out of the inner lumen of the pusher, for example, as the pusher is withdrawn from the alimentary canal following a plug placement procedure.

In certain aspects, this sort of pusher will also include an adaptation for feeding or otherwise guiding the guidewire into this longitudinal side wall opening after the guidewire exits the wire channel side opening. Illustratively, an outer sleeve, which includes a small tongue or tooth that is angled inward toward the side opening, can be placed distal to the wire channel side opening. When moved proximal, the sleeve can then push the wire that exits the wire channel side opening through the longitudinal side wall opening and into the inner lumen of the pusher.

Figure 14:
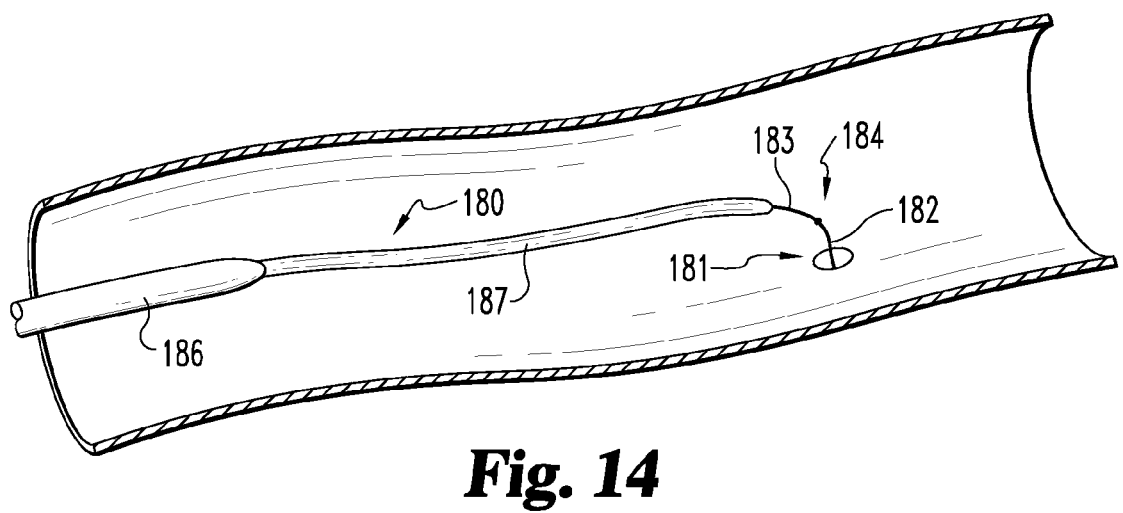
FIG. 14 depicts a step of another illustrative inventive method and components of inventive devices and apparatuses.

With reference now to FIG. 14, shown are parts of another illustrative fistula plug delivery system 180 of the invention at a location in the alimentary canal near a primary fistula opening 181. System 180 includes a plug-guiding device comprised of a first endoluminally advanceable device 182 and a second endoluminally advanceable device 183. The distal end of device 182, which is shown extending a distance out from primary opening 181 is coupled to or otherwise joined with (e.g., magnetically, using a coupling mechanism, etc.) the distal end of device 183 at a coupling point 184. A fistula tract extends from primary opening 181, and device 182 is positioned in this tract with its proximal end (not shown) extending a distance out from a secondary fistula opening. The part of device 183 that is not shown in FIG. 14 extends back through the alimentary canal such that its proximal end exits a natural opening in the canal. In this regard, the plug-guiding device extends continuously through the body from the secondary fistula opening to the mouth or anus. To provide the type of arrangement shown in FIG. 14, device 182 and device 183 can be delivered into position in any suitable manner including any of those described herein.

A fistula plug comprising a plug body 186 is received over device 183. In this specific illustrative embodiment, plug body 186 is generally cylindrical yet tapers to a rounded tip at its distal end, although any of the fistula plugs described herein including those housed in a delivery housing, sheath, etc. and those additionally or alternatively providing some sort of capping arrangement, etc. could be utilized in this regard. Thus, plug body 186 can be substituted with a plug delivery device such as those shown in FIGS. 3 and 10 or any of the other delivery devices described herein. As well, advancing plug body 186 to such a location in the body can be accomplished in any suitable manner. Illustratively, a pushing element such as either of those shown in FIGS. 3 and 13 or any of the others described herein can be employed.

Continuing with FIG. 14, a leading member 187 is attached to and extends distally from plug body 186. Leading member 187 has a central longitudinal lumen extending therethrough, and thus, can also be received over the plug-guiding device for advancement through the body. Leading member 187 can be formed with a variety of materials, although it is preferable that the material used provides sufficient column strength for the member to be pushed through the body without undesirably buckling or kinking. In one embodiment, a leading member extending from a plug body (or a delivery vehicle that is housing a plug body) will comprise a sheath such a Flexor sheath available from Cook Urological, Inc., 1100 West Morgan Street, P.O. Box 227 Spencer, Ind. 47460. In this and other embodiments, the leading member may be progressively more flexible toward its distal tip to facilitate entry into the primary opening.

Leading member 187 can be advanced into and through the fistula tract through primary opening 181, for example, so that by the time the distal end of plug body 186 reaches the primary opening, leading member 187 is extending out of the secondary opening. In this way, leading member 187 may be used to at least help advance plug body 186 into and through the fistula tract, e.g., by providing a means for pulling the plug into the tract. Such a leading member may additionally be useful to help guide and ease the distal end of the plug into the fistula opening. Leading members exhibiting a variety of other shapes and configurations are also contemplated, and include some that can be received over a guidewire or similar device and some that cannot. Those not received over a guidewire, in certain embodiments, will be associated with the wire so that the member can translate along the wire, for example, in the case of a leading wire having one end that is attached to the plug body and another end that can move along the wire. Advantageous leading members, in some forms, will be configured to assist in advancing a plug body into and/or through a fistula tract, and will exhibit desirable physical and mechanical properties in order to do so.

As disclosed above, the present invention also provides methods and apparatuses that involve delivering a fistula plug into a fistula tract through a secondary fistula opening and toward a primary fistula opening. Illustratively, a fistula plug can be pulled through a secondary opening and toward a primary fistula opening with a pulling device coupled to the fistula plug. In one inventive method, the distal portion of a first wire (e.g., while residing in an endoscope or other suitable endoluminal advancable device) is advanced through the alimentary canal and to the primary fistula opening. The distal portion of a second wire is advanced through the fistula tract from the secondary fistula opening to the primary fistula opening. A fistula plug is coupled to or otherwise associated with a proximal portion of the second wire. Thereafter, the distal portions of the two wires are suitably united, and the first-wire distal portion is withdrawn back through the alimentary canal, pulling the second wire, and thus the fistula plug, therealong. The fistula plug can be pulled into the tract a suitable distance, e.g., with an end of the plug residing at or near the primary opening. In one aspect, a fistula graft including a capping member is pulled through the fistula tract until the capping member passes through the primary opening and into the alimentary canal. Thereafter, the capping member can be caused or allowed to expand, and if necessary, the graft can be repositioned so that the capping member contacts portions of the alimentary canal wall adjacent to the primary opening. Additionally or alternatively, a fistula graft can be configured to translate along a plug-guiding device (e.g., a guidewire) extending through the fistula tract. Such a plug-guiding device can be positioned in the fistula tract in any suitable manner including any of those described herein. The fistula graft can then be pushed and/or pulled into the fistula tract from the secondary opening to the primary opening along this plug-guiding device until desirably placed.

In certain aspects of the invention, treatment of a fistula includes an endoscopic visualization (fistuloscopy) step that is performed prior to implanting a fistula plug. Such endoscopic visualization can be used, for example, to determine the shape and size of a fistula, which in turn can be used to select an appropriately sized and shaped fistula graft device for treating the fistula. Illustratively, a very thin flexible endoscope can be inserted into a secondary opening of the fistula and advanced under direct vision through the fistula tract and out through the primary opening. By performing fistuloscopy of the fistula, the primary opening can be accurately identified. Also, certain fistula treatment methods of the invention include a fistula cleaning step that is performed prior to implanting a fistula graft. For example, an irrigating fluid can be used to remove any inflammatory or necrotic tissue located within the fistula prior to engrafting the graft device. In certain embodiments, one or more antibiotics are applied to the fistula graft device and/or the soft tissues surrounding the fistula as an extra precaution or means of treating any residual infection within the fistula.

Further, the delivery systems and methods of the present invention can be adapted for delivering fistula grafts into multiple fistula tracts in a given medical procedure. In this context, the term "fistula tract" is meant to include, but is not limited to, a void in soft tissues extending from a primary fistula opening, whether blind-ending or leading to one or more secondary fistula openings, for example, to include what are generally described as simple and complex fistulae. In cases of complex fistulae, for example a horse-shoe fistula, there may be one primary opening and two or more fistula tracts extending from that opening. In such instances, a fistula graft may be delivered to any of the fistula tracts.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method of treating an enterocutaneous fistula in a patient, the fistula having at least a primary fistula opening in a bowel wall, a secondary fistula opening in skin of the patient, and a fistula tract extending therebetween, the method comprising:
advancing an endoscope into the alimentary canal of the patient from a natural body opening of the patient;
providing a first wire through the endoscope, the first wire having a distal portion;
advancing a second wire through the fistula tract from the secondary fistula opening to and out of the primary fistula opening to position a distal portion of the second wire in the alimentary canal;
joining the distal portion of the second wire with the distal portion of the first wire; withdrawing the first wire back out of the alimentary canal so as to leave the second wire emplaced in the patient;
associating a fistula plug assembly comprising a fistula plug with at least a portion residing in a protective housing having a rounded tip with the second wire; and
pulling the second wire to pull the fistula plug assembly through the bowel of the patient, through the primary fistula opening, and into the fistula tract.

2. The method of claim 1, wherein the natural body opening is the mouth.

3. The method of claim 1, wherein the natural body opening is the anus.

4. The method of claim 1, wherein the protective housing is separable.

5. The method of claim 1, wherein the protective housing comprises a capsule.

6. The method of claim 1, wherein the fistula plug is comprised of an extracellular matrix material.

7. The method of claim 6, wherein the extracellular matrix material comprises porcine submucosa.

8. A method of treating an enterocutaneous fistula having at least a primary fistula opening in a bowel wall, a secondary fistula opening in skin of a patient, and a fistula tract extending therebetween, the method comprising:
providing a retrieving device having a distal portion;
providing a plug-guiding device having a distal portion and a proximal portion;
providing a fistula plug assembly comprising a fistula plug with at least a portion residing in a protective housing;
advancing the retrieving device distal portion through the fistula tract from the secondary fistula opening to the primary fistula opening;
advancing the plug-guiding device distal portion from a natural body opening in the alimentary canal of the patient, through the alimentary canal and to the primary fistula opening; wherein the proximal portion of the plug-guiding device extends out of the natural body opening;
directly joining within the patient the plug-guiding device distal portion to the retrieving device distal portion;
withdrawing the retrieving device distal portion back through the fistula tract from the primary fistula opening to the secondary fistula opening, wherein the coupled plug-guiding device distal portion is pulled therealong to the secondary fistula opening and wherein the proximal portion of the plug-guiding device that extends out of the natural body opening is pulled into the alimentary canal; and
pulling the plug-guiding device to pull the fistula plug assembly through the bowel of the patient and into the fistula tract through the primary fistula opening;
wherein the plug-guiding device is a steerable guidewire.

9. The method of claim 8, wherein the protective housing is separable.

10. The method of claim 8, wherein the protective housing has a rounded tip.

11. The method of claim 8, wherein the fistula plug is comprised of an extracellular matrix material.

12. The method of claim 11, wherein the extracellular matrix material comprises porcine submucosa.

13. The method of claim 8, wherein advancing the plug-guiding device distal portion through the alimentary canal to the primary fistula opening includes pushing the plug-guiding device through a natural body opening to a point at or near the primary fistula opening.

14. The method of claim 13, wherein the natural body opening is the mouth.

15. The method of claim 14, wherein the natural body opening is the anus.

16. The method of claim 8, wherein the protective housing comprises a capsule.

17. A method of treating an enterocutaneous fistula having at least a primary fistula opening in a bowel wall, a secondary fistula opening in skin of a patient, and a fistula tract extending therebetween, the method comprising:
providing a first elongate device having a distal portion and a proximal portion;
providing a second elongate device having a distal portion and a proximal portion;
providing a fistula plug assembly comprising a fistula plug with at least a portion residing in a protective housing;
advancing the distal portion of the first elongate device through the fistula tract from the secondary fistula opening to a point at or near the primary fistula opening;
advancing the distal portion of the second elongate device through a natural body opening of the patient to said point at or near the primary fistula opening, wherein the proximal portion of the second elongate device extends out of the natural body opening when the distal portion of the second elongate device is positioned at said point at or near the primary fistula opening;
directly joining the distal portion of the first elongate device to the distal portion of the second elongate device to provide a plug-guiding device along which the fistula plug can be advanced; and
advancing the fistula plug assembly along the plug-guiding device into the fistula tract;
wherein the second elongate device is a steerable guidewire.

18. The method of claim 17, wherein the fistula plug is delivered into the fistula tract through the primary fistula opening.

19. The method of claim 17, wherein the fistula plug is delivered into the fistula tract through the secondary fistula opening.

20. The method of claim 17, wherein the natural body opening is the mouth.

21. The method of claim 17, wherein the natural body opening is the anus.

22. The method of claim 17, wherein the protective housing is separable.

23. The method of claim 17, wherein the protective housing comprises a capsule.

24. The method of claim 17, wherein the fistula plug is comprised of an extracellular matrix material.

25. The method of claim 24, wherein the extracellular matrix material comprises porcine submucosa.

26. A method of treating an enterocutaneous fistula having at least a primary fistula opening in a bowel wall, a secondary fistula opening in skin of a patient, and a fistula tract extending therebetween, the method comprising:
   providing a plug-guiding device configured to traverse the fistula tract and a portion of the bowel of the patient;
   providing a fistula plug delivery apparatus translatable along the plug-guiding device and including a fistula plug residing in a protective housing and a pushing element, the pushing element effective to push the fistula plug and protective housing through the bowel;
   positioning the plug-guiding device through the fistula tract and through a portion of the bowel, wherein said positioning comprises (i) advancing the plug-guiding device from a natural body opening of the patient to the bowel through the bowel to position a distal portion of the plug-guiding device adjacent to the primary fistula opening in the bowel wall, wherein a proximal portion of the plug-guiding device extends out of the natural body opening when the distal portion of the plug-guiding device is adjacent to the primary fistula opening, (ii) directly joining within the patient the distal portion of the plug-guiding device with a distal portion of a retrieval device extended through the fistula tract, and (iii) pulling the retrieval device to pull the distal portion of the plug-guiding device through the primary opening of the fistula, through the fistula tract, and out of the secondary opening of the fistula;
   pushing the fistula plug delivery apparatus along the plug-guiding device through the bowel to the primary fistula opening with the pushing element, wherein the fistula plug resides in the protective housing; and
   pushing the fistula plug and the protective housing along the plug-guiding device through the fistula tract toward the secondary fistula opening;
   wherein the plug-guiding device is a steerable guidewire.

27. The method of claim 26, wherein the fistula plug is receivable over the plug-guiding device.

28. The method of claim 27, wherein the pushing element is receivable over the plug-guiding device.

29. The method of claim 26, wherein the pushing element is receivable over the plug-guiding device.

30. The method of claim 26, wherein the fistula plug and the pushing element are unconnected.

31. The method of claim 26, wherein the fistula plug and the pushing element are releasably connected.

32. The method of claim 26, wherein the pushing element extends through at least part of the fistula plug.

33. The method of claim 26, wherein:
   the protective housing is separable.

34. The method of claim 26, wherein:
   the protective housing has a rounded tip.

35. The method of claim 26, wherein the fistula plug is comprised of an extracellular matrix material.

36. The method of claim 35, wherein the extracellular matrix material comprises porcine submucosa.

37. A method for treating an enterocutaneous fistula having a primary opening in an intestine of the alimentary canal of a patient and a secondary opening at skin of the patient, the method comprising:
   delivering a fistula graft with at least a portion residing in a protective housing into the alimentary canal through a natural body opening of the patient, the fistula graft including a capping member and a plug body that extends from the capping member;
   inserting a pulling element through the fistula from the secondary opening to and out of the primary opening, uniting the pulling element with a wire, and then pulling the pulling element through the alimentary canal by pulling the wire back out of the alimentary canal;
   pulling the plug body and the protective housing through the alimentary canal toward the primary opening of the fistula with the pulling element that extends to the plug body from the primary opening of the fistula; and
   pulling the plug body with at least a portion residing in the protective housing from the intestine of the alimentary canal into the fistula through the primary opening by pulling the pulling element until the capping member which is trailing the plug body contacts patient tissue adjacent the primary opening for blocking the primary opening.

38. The method of claim 37, wherein the natural body opening is the mouth.

39. The method of claim 37, wherein the natural body opening is the anus.

40. The method of claim 37, wherein the protective housing is separable.

41. The method of claim 38, wherein the protective housing has a rounded tip.

* * * * *